(12) United States Patent
Marchand et al.

(10) Patent No.: US 9,844,387 B2
(45) Date of Patent: *Dec. 19, 2017

(54) INTRAVASCULAR TREATMENT OF VASCULAR OCCLUSION AND ASSOCIATED DEVICES, SYSTEMS, AND METHODS

(71) Applicant: Inari Medical, Inc., Irvine, CA (US)

(72) Inventors: Phil Marchand, Lake Forest, CA (US); John C. Thress, Capistrano Beach, CA (US); Jacob F. Louw, Carlsbad, CA (US); Brian J. Cox, Laguna Nigel, CA (US); Richard Quick, Mission Viejo, CA (US)

(73) Assignee: INARI MEDICAL, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,426

(22) Filed: Jun. 5, 2017

(65) Prior Publication Data

US 2017/0265878 A1     Sep. 21, 2017

Related U.S. Application Data

(63) Continuation of application No. 15/268,296, filed on Sep. 16, 2016, now Pat. No. 9,700,332.

(Continued)

(51) Int. Cl.
*A61B 17/221* (2006.01)
*A61F 2/01* (2006.01)
*A61B 17/22* (2006.01)

(52) U.S. Cl.
CPC .......... *A61B 17/221* (2013.01); *A61F 2/013* (2013.01); *A61B 2017/2212* (2013.01); *A61B 2017/22041* (2013.01)

(58) Field of Classification Search
CPC .. A61F 2/011; A61F 2/013; A61F 2002/0111; A61F 2002/016;

(Continued)

(56) References Cited

U.S. PATENT DOCUMENTS 2,955,592 A  10/1960  Maclean et al.
3,435,826 A   5/1964  Fogarty
(Continued)

FOREIGN PATENT DOCUMENTS

EP   1867290 B1   12/2007
JP   6190049       7/1994
(Continued)

OTHER PUBLICATIONS

Gibbs, et al., "Temporary Stent as a bail-out device during percutaneous transluminal coronary angioplasty: preliminary clinical experience," British Heart Journal, 1994, 71:372-377, Oct. 12, 1993, 6 pages.
Goldhaber, S. et al. "Percutaneous Mechanical Thrombectomy for Acute Pulmonary Embolism—A Double-Edged Sword", American College of Chest Physicians, Aug. 2007: 132:2, 363-372.
Goldhaber, S., "Advanced treatment strategies for acute pulmonary embolism, including thrombolysis and embolectomy", Journal of Thrombosis and Haemostasis, 2009: 7 (Suppl. 1): 322-327.
Gupta, S. et al., "Acute Pulmonary Embolism Advances in Treatment", JAPI, Association of Physicians India, Mar. 2008, vol. 56, 185-191.
(Continued)

*Primary Examiner* — David C Eastwood
(74) *Attorney, Agent, or Firm* — Kilpatrick Townsend & Stockton LLP

(57) ABSTRACT

Systems and methods for treating thrombosis and or emboli in a peripheral vasculature of a patient are disclosed herein. The method can include providing a thrombus extraction device including a proximal self-expanding coring portion formed of a unitary fenestrated structure and a distal expandable tubular portion formed of a braided filament mesh structure; advancing a catheter constraining the thrombus extraction device through a vascular thrombus in a vessel; deploying the thrombus extraction device from the catheter from a constrained configuration to an expanded configuration; retracting the thrombus extraction device proximally so that the coring portion cores and separates a portion of the vascular thrombus from the venous vessel wall while the mesh structure captures the vascular thrombus portion; and withdrawing the thrombus extraction device from the patient to remove the vascular thrombus portion from the vessel.

28 Claims, 20 Drawing Sheets

Related U.S. Application Data

(60) Provisional application No. 62/245,935, filed on Oct. 23, 2015.

(58) Field of Classification Search
CPC ......... A61F 2002/018; A61B 17/22012; A61B 2017/22034; A61B 17/3207; A61B 2017/320716; A61B 17/320725; A61B 2017/320733; A61B 17/32075; A61B 17/221; A61B 2017/220011; A61B 2017/22002
See application file for complete search history.

(56) References Cited

U.S. PATENT DOCUMENTS

| | | | |
|---|---|---|---|
| 3,923,065 A | 12/1975 | Nozick et al. | |
| 4,030,503 A | 6/1977 | Clark, III | |
| 4,650,466 A | 3/1987 | Luther et al. | |
| 4,873,978 A | 10/1989 | Ginsburg | |
| 4,883,458 A | 11/1989 | Shiber | |
| 4,890,611 A | 1/1990 | Monfort et al. | |
| 5,011,488 A | 4/1991 | Ginsburg | |
| 5,059,178 A | 10/1991 | Ya | |
| 5,100,423 A | 3/1992 | Fearnot et al. | |
| 5,102,415 A | 4/1992 | Guenther et al. | |
| 5,129,910 A | 7/1992 | Phan et al. | |
| 5,192,286 A | 3/1993 | Phan et al. | |
| 5,192,290 A | 3/1993 | Hilal | |
| 5,364,345 A | 11/1994 | Lowery et al. | |
| 5,370,653 A | 12/1994 | Cragg | |
| 5,443,443 A | 8/1995 | Shiber et al. | |
| 5,476,450 A | 12/1995 | Ruggio | |
| 5,490,859 A | 2/1996 | Mische et al. | |
| 5,746,758 A | 5/1998 | Nordgren et al. | |
| 5,749,858 A | 5/1998 | Cramer | |
| 5,766,191 A | 6/1998 | Trerotola et al. | |
| 5,827,304 A | 10/1998 | Hart | |
| 5,868,708 A | 2/1999 | Hart et al. | |
| 5,873,882 A | 2/1999 | Straub et al. | |
| 5,876,414 A | 3/1999 | Straub et al. | |
| 5,882,329 A | 3/1999 | Patterson et al. | |
| 5,902,263 A | 5/1999 | Patterson et al. | |
| 5,941,869 A | 8/1999 | Patterson et al. | |
| 5,972,019 A | 10/1999 | Engelson et al. | |
| 6,066,149 A | 5/2000 | Samson et al. | |
| 6,066,158 A | 5/2000 | Engelson et al. | |
| 6,152,946 A | 11/2000 | Broome et al. | |
| 6,168,579 B1 | 1/2001 | Tsugita et al. | |
| 6,203,561 B1 | 3/2001 | Ramee et al. | |
| 6,221,006 B1 | 4/2001 | Dubrul et al. | |
| 6,238,412 B1 | 5/2001 | Dubrul et al. | |
| 6,254,571 B1 | 7/2001 | Hart | |
| 6,258,115 B1 | 7/2001 | Dubrul et al. | |
| 6,364,895 B1 | 4/2002 | Greenhalgh et al. | |
| 6,371,970 B1 * | 4/2002 | Khosravi | A61F 2/01 606/194 |
| 6,383,205 B1 | 5/2002 | Samson et al. | |
| 6,413,235 B1 | 7/2002 | Parodi et al. | |
| 6,423,032 B2 | 7/2002 | Parodi et al. | |
| 6,440,148 B1 | 8/2002 | Shiber et al. | |
| 6,454,775 B1 | 9/2002 | Demarais et al. | |
| 6,458,139 B1 | 10/2002 | Palmer et al. | |
| 6,511,492 B1 | 1/2003 | Rosenbluth et al. | |
| 6,514,273 B1 | 2/2003 | Voss et al. | |
| 6,530,935 B2 | 3/2003 | Wensel et al. | |
| 6,530,939 B1 | 3/2003 | Hopkins et al. | |
| 6,544,279 B1 | 4/2003 | Hopkins et al. | |
| 6,589,263 B1 | 7/2003 | Hopkins et al. | |
| 6,596,011 B2 | 7/2003 | Johnson et al. | |
| 6,602,271 B2 | 8/2003 | Adams et al. | |
| 6,605,102 B1 | 8/2003 | Mazzocchi et al. | |
| 6,635,070 B2 | 10/2003 | Leeflang et al. | |
| 6,645,222 B1 | 11/2003 | Parodi et al. | |
| 6,660,013 B2 | 12/2003 | Rabiner et al. | |
| 6,663,650 B2 | 12/2003 | Sepetka et al. | |
| 6,685,722 B1 | 2/2004 | Rosenbluth et al. | |
| 6,699,260 B2 | 3/2004 | Dubrul et al. | |
| 6,755,722 B1 | 6/2004 | Horie et al. | |
| 6,755,847 B2 | 6/2004 | Eskuri et al. | |
| 6,767,353 B1 | 7/2004 | Shiber | |
| 6,800,080 B1 | 10/2004 | Bates et al. | |
| 6,939,361 B1 | 9/2005 | Kleshinski | |
| 6,960,222 B2 | 11/2005 | Vo et al. | |
| 7,004,954 B1 | 2/2006 | Voss et al. | |
| 7,036,707 B2 | 5/2006 | Ezumi et al. | |
| 7,052,500 B2 | 5/2006 | Bashiri et al. | |
| 7,056,328 B2 | 6/2006 | Arnott et al. | |
| 7,179,273 B1 | 2/2007 | Palmer et al. | |
| 7,220,269 B1 | 5/2007 | Ansel et al. | |
| 7,232,432 B2 | 6/2007 | Fulton et al. | |
| 7,244,243 B2 | 7/2007 | Lary | |
| 7,285,126 B2 | 10/2007 | Sepetka et al. | |
| 7,306,618 B2 | 12/2007 | Demond et al. | |
| 7,320,698 B2 | 1/2008 | Eskuri | |
| 7,323,002 B2 | 1/2008 | Johnson et al. | |
| 7,331,980 B2 | 2/2008 | Dubrul et al. | |
| 7,578,830 B2 | 8/2009 | Kusleika et al. | |
| 7,621,870 B2 | 11/2009 | Berrada et al. | |
| 7,691,121 B2 | 4/2010 | Rosenbluth et al. | |
| 7,763,010 B2 | 7/2010 | Strang et al. | |
| 7,766,934 B2 | 8/2010 | Pal et al. | |
| 7,905,896 B2 | 3/2011 | Straub et al. | |
| 7,938,820 B2 | 5/2011 | Webster et al. | |
| 7,993,302 B2 | 8/2011 | Hebert et al. | |
| 7,993,363 B2 | 8/2011 | Demond et al. | |
| 8,006,757 B2 | 8/2011 | Hackworth et al. | |
| 8,043,313 B2 | 10/2011 | Krolik et al. | |
| 8,052,640 B2 | 11/2011 | Fiorella et al. | |
| 8,066,757 B2 | 11/2011 | Ferrera et al. | |
| 8,070,791 B2 | 12/2011 | Ferrera et al. | |
| 8,075,510 B2 | 12/2011 | Aklog et al. | |
| 8,088,140 B2 | 1/2012 | Ferrera et al. | |
| 8,100,935 B2 | 1/2012 | Rosenbluth et al. | |
| 8,109,962 B2 | 2/2012 | Pal et al. | |
| 8,118,829 B2 | 2/2012 | Carrison et al. | |
| 8,197,493 B2 | 6/2012 | Ferrera et al. | |
| 8,246,641 B2 | 8/2012 | Osborne et al. | |
| 8,261,648 B1 | 9/2012 | Marchand et al. | |
| 8,298,257 B2 | 10/2012 | Sepetka et al. | |
| 8,317,748 B2 | 11/2012 | Fiorella et al. | |
| RE43,902 E | 1/2013 | Hopkins et al. | |
| 8,357,178 B2 | 1/2013 | Grandfield et al. | |
| 8,361,104 B2 | 1/2013 | Jones et al. | |
| 8,409,215 B2 | 4/2013 | Sepetka et al. | |
| 8,486,105 B2 | 7/2013 | Demond et al. | |
| 8,512,352 B2 | 8/2013 | Martin et al. | |
| 8,535,334 B2 | 9/2013 | Martin et al. | |
| 8,545,526 B2 | 10/2013 | Martin et al. | |
| 8,568,432 B2 | 10/2013 | Straub et al. | |
| 8,574,262 B2 | 11/2013 | Ferrera et al. | |
| 8,579,915 B2 | 11/2013 | French et al. | |
| 8,585,713 B2 | 11/2013 | Ferrera et al. | |
| 8,696,622 B2 | 4/2014 | Fiorella et al. | |
| 8,784,434 B2 | 7/2014 | Rosenbluth et al. | |
| 8,784,441 B2 | 7/2014 | Rosenbluth et al. | |
| 8,795,305 B2 | 8/2014 | Martin et al. | |
| 8,795,345 B2 | 8/2014 | Martin et al. | |
| 8,801,748 B2 | 8/2014 | Martin et al. | |
| 8,820,207 B2 | 9/2014 | Marchand et al. | |
| 8,826,791 B2 | 9/2014 | Thompson et al. | |
| 8,828,044 B2 | 9/2014 | Aggerholm et al. | |
| 8,833,224 B2 | 9/2014 | Thompson et al. | |
| 8,852,205 B2 | 10/2014 | Brady et al. | |
| 8,852,226 B2 | 10/2014 | Gilson et al. | |
| 8,932,319 B2 | 1/2015 | Martin et al. | |
| 8,945,143 B2 | 2/2015 | Ferrera et al. | |
| 8,945,172 B2 | 2/2015 | Ferrera et al. | |
| 8,992,504 B2 | 3/2015 | Castella et al. | |
| 9,149,609 B2 | 10/2015 | Ansel et al. | |
| 9,161,766 B2 | 10/2015 | Slee et al. | |
| 9,204,887 B2 | 12/2015 | Cully et al. | |
| 9,283,066 B2 | 3/2016 | Hopkins et al. | |
| 9,351,749 B2 * | 5/2016 | Brady | A61B 17/221 |
| 9,402,708 B2 * | 8/2016 | Holloway | A61F 2/013 |

(56) References Cited

U.S. PATENT DOCUMENTS

| | | | |
|---|---|---|---|
| 9,427,252 B2* | 8/2016 | Sos | A61B 17/221 |
| 9,439,664 B2* | 9/2016 | Sos | A61B 17/221 |
| 9,445,829 B2* | 9/2016 | Brady | A61B 17/12109 |
| 9,456,834 B2* | 10/2016 | Folk | A61B 17/221 |
| 9,463,036 B2* | 10/2016 | Brady | A61B 17/221 |
| 9,700,332 B2* | 7/2017 | Marchand | A61B 17/32072 |
| 9,757,137 B2 | 9/2017 | Krolik et al. | |
| 2002/0022858 A1 | 2/2002 | Demond et al. | |
| 2002/0026211 A1 | 2/2002 | Khosravi et al. | |
| 2002/0147458 A1 | 10/2002 | Hiblar et al. | |
| 2003/0100919 A1 | 5/2003 | Hopkins et al. | |
| 2003/0114875 A1 | 6/2003 | Sjostrom et al. | |
| 2003/0191516 A1 | 10/2003 | Weldon et al. | |
| 2004/0068288 A1* | 4/2004 | Palmer | A61B 17/221 606/200 |
| 2004/0068314 A1* | 4/2004 | Jones | A61B 17/12022 623/1.15 |
| 2004/0073243 A1 | 4/2004 | Sepetka et al. | |
| 2004/0133232 A1 | 7/2004 | Rosenbluth et al. | |
| 2004/0167567 A1 | 8/2004 | Cano et al. | |
| 2004/0199201 A1 | 10/2004 | Kellett et al. | |
| 2005/0055047 A1 | 3/2005 | Greenhalgh | |
| 2005/0119668 A1 | 6/2005 | Teague et al. | |
| 2006/0020286 A1 | 1/2006 | Niermann et al. | |
| 2006/0047286 A1 | 3/2006 | West et al. | |
| 2006/0224177 A1 | 10/2006 | Finitsis | |
| 2006/0229645 A1 | 10/2006 | Bonnette et al. | |
| 2006/0282111 A1 | 12/2006 | Morsi | |
| 2007/0118165 A1 | 5/2007 | DeMello et al. | |
| 2007/0161963 A1 | 7/2007 | Smalling | |
| 2007/0179513 A1 | 8/2007 | Deutsch | |
| 2007/0191866 A1 | 8/2007 | Palmer et al. | |
| 2007/0198028 A1 | 8/2007 | Miloslavski et al. | |
| 2007/0208361 A1 | 9/2007 | Okushi et al. | |
| 2007/0208367 A1 | 9/2007 | Fiorella et al. | |
| 2007/0213753 A1 | 9/2007 | Waller | |
| 2007/0255252 A1 | 11/2007 | Mehta | |
| 2007/0288054 A1* | 12/2007 | Tanaka | A61B 17/221 606/200 |
| 2008/0167678 A1 | 7/2008 | Morsi | |
| 2008/0228209 A1 | 9/2008 | DeMello et al. | |
| 2008/0255596 A1* | 10/2008 | Jenson | A61B 17/221 606/159 |
| 2008/0269798 A1 | 10/2008 | Ramzipoor et al. | |
| 2009/0054918 A1 | 2/2009 | Henson | |
| 2009/0062841 A1 | 3/2009 | Amplatz et al. | |
| 2009/0069828 A1 | 3/2009 | Martin et al. | |
| 2009/0163846 A1 | 6/2009 | Aklog et al. | |
| 2009/0182362 A1 | 7/2009 | Thompson et al. | |
| 2009/0292307 A1 | 11/2009 | Razack | |
| 2009/0299393 A1 | 12/2009 | Martin et al. | |
| 2010/0087850 A1* | 4/2010 | Razack | A61B 17/221 606/200 |
| 2010/0087908 A1* | 4/2010 | Hilaire | A61F 2/013 623/1.11 |
| 2010/0114113 A1 | 5/2010 | Dubrul et al. | |
| 2010/0249815 A1 | 9/2010 | Jantzen et al. | |
| 2010/0268264 A1 | 10/2010 | Bonnette et al. | |
| 2010/0318178 A1 | 12/2010 | Rapaport et al. | |
| 2011/0009950 A1* | 1/2011 | Grandfield | A61F 2/91 623/1.16 |
| 2011/0060212 A1 | 3/2011 | Slee et al. | |
| 2011/0152993 A1 | 6/2011 | Marchand et al. | |
| 2011/0190806 A1 | 8/2011 | Wittens | |
| 2011/0196414 A1* | 8/2011 | Porter | A61B 17/221 606/200 |
| 2011/0213290 A1 | 9/2011 | Chin et al. | |
| 2011/0213403 A1 | 9/2011 | Aboytes | |
| 2011/0224707 A1 | 9/2011 | Miloslavski et al. | |
| 2011/0251629 A1 | 10/2011 | Galdonik et al. | |
| 2011/0264133 A1 | 10/2011 | Hanlon et al. | |
| 2012/0022634 A1* | 1/2012 | Kusleika | A61L 29/02 623/1.11 |
| 2012/0059309 A1* | 3/2012 | di Palma | A61B 17/12186 604/22 |
| 2012/0059356 A1* | 3/2012 | di Palma | A61B 17/221 604/509 |
| 2012/0089216 A1 | 4/2012 | Rapaport et al. | |
| 2012/0101510 A1 | 4/2012 | Lenker et al. | |
| 2012/0143239 A1 | 6/2012 | Aklog et al. | |
| 2012/0165919 A1 | 6/2012 | Cox et al. | |
| 2012/0179181 A1 | 7/2012 | Straub et al. | |
| 2012/0232655 A1 | 9/2012 | Lorrison et al. | |
| 2012/0271231 A1 | 10/2012 | Agrawal | |
| 2012/0277788 A1 | 11/2012 | Cattaneo et al. | |
| 2013/0066348 A1 | 3/2013 | Fiorella et al. | |
| 2013/0144326 A1 | 6/2013 | Brady et al. | |
| 2013/0165871 A1 | 6/2013 | Fiorella et al. | |
| 2013/0197567 A1* | 8/2013 | Brady | A61B 17/221 606/200 |
| 2013/0317589 A1 | 11/2013 | Martin et al. | |
| 2013/0345739 A1 | 12/2013 | Brady et al. | |
| 2014/0005712 A1 | 1/2014 | Martin et al. | |
| 2014/0005713 A1 | 1/2014 | Bowman | |
| 2014/0005715 A1 | 1/2014 | Castella et al. | |
| 2014/0005717 A1 | 1/2014 | Martin et al. | |
| 2014/0031856 A1 | 1/2014 | Martin et al. | |
| 2014/0046243 A1* | 2/2014 | Ray | A61B 17/22012 604/22 |
| 2014/0046244 A1* | 2/2014 | Ray | A61B 17/22012 604/22 |
| 2014/0121672 A1* | 5/2014 | Folk | A61F 2/013 606/127 |
| 2014/0180397 A1 | 6/2014 | Gerberding et al. | |
| 2014/0188143 A1 | 7/2014 | Martin et al. | |
| 2014/0194911 A1* | 7/2014 | Johnson | A61B 17/221 606/159 |
| 2014/0236219 A1* | 8/2014 | Dubrul | A61B 10/0266 606/200 |
| 2014/0243882 A1 | 8/2014 | Ma et al. | |
| 2014/0318354 A1 | 10/2014 | Thompson et al. | |
| 2014/0364896 A1* | 12/2014 | Consigny | A61B 17/3207 606/200 |
| 2015/0018929 A1 | 1/2015 | Martin et al. | |
| 2015/0025555 A1* | 1/2015 | Sos | A61B 17/221 606/159 |
| 2015/0032144 A1* | 1/2015 | Holloway | A61F 2/013 606/200 |
| 2015/0127035 A1 | 5/2015 | Trapp et al. | |
| 2015/0133990 A1* | 5/2015 | Davidson | A61N 1/378 606/200 |
| 2015/0150672 A1 | 6/2015 | Ma et al. | |
| 2015/0190156 A1 | 7/2015 | Ulm et al. | |
| 2015/0196380 A1 | 7/2015 | Berrada et al. | |
| 2015/0196744 A1 | 7/2015 | Aboytes et al. | |
| 2015/0209058 A1 | 7/2015 | Ferrera et al. | |
| 2015/0209165 A1 | 7/2015 | Grandfield et al. | |
| 2015/0238207 A1 | 8/2015 | Cox et al. | |
| 2015/0250578 A1 | 9/2015 | Cook et al. | |
| 2015/0265299 A1 | 9/2015 | Cooper et al. | |
| 2015/0297251 A1* | 10/2015 | Sos | A61B 17/221 606/159 |
| 2016/0030155 A1 | 2/2016 | Cox et al. | |
| 2016/0066933 A1* | 3/2016 | Root | A61B 17/221 606/194 |
| 2016/0367285 A1* | 12/2016 | Sos | A61B 17/22032 |

FOREIGN PATENT DOCUMENTS

| | | |
|---|---|---|
| JP | 2004097807 | 4/2004 |
| JP | 2005-095242 | 4/2005 |
| JP | 2005230132 | 9/2005 |
| JP | 2005323702 | 11/2005 |
| JP | 2006094876 | 4/2006 |
| WO | WO-1997017889 | 5/1997 |
| WO | WO 98/38920 A1 | 9/1998 |
| WO | WO 1999044542 A2 | 9/1999 |
| WO | WO 03/015840 A2 | 2/2003 |
| WO | WO 2004/093696 A1 | 11/2004 |
| WO | WO-2005046736 | 5/2005 |
| WO | WO-2006110186 | 10/2006 |

(56) References Cited

FOREIGN PATENT DOCUMENTS

| WO | WO-2007092820 | 8/2007 |
|---|---|---|
| WO | WO-2009155571 | 12/2009 |
| WO | WO-2010010545 | 1/2010 |
| WO | WO-2010023671 | 3/2010 |
| WO | WO-2010049121 | 5/2010 |
| WO | WO-2010102307 | 9/2010 |
| WO | WO-2011054531 | 5/2011 |
| WO | WO-2012009675 | 1/2012 |
| WO | WO 2012011097 A1 | 1/2012 |
| WO | WO-2012065748 | 5/2012 |
| WO | WO-2014047650 | 3/2014 |
| WO | WO-2014081892 | 5/2014 |

OTHER PUBLICATIONS

Konstantinides, S. et al., "Pulmonary embolism: risk assessment and management", European Society of Cardiology European Heart Journal, Sep. 7, 2012:33, 3014-3022.

Konstantinides, S. et al., "Pulmonary embolism hotline 2012—Recent and expected trials", Thrombosis and Haemostasis, Jan. 9, 2013:33 43-50.

Kucher, N. et al., "Percutaneous Catheter Thrombectomy Device for Acute Pulmonary Embolism: In Vitro and in Vivo Testing", Circulation, Sep. 2005:112: e28-e32.

Kucher, N. et al., "Management of Massive Pulmonary Embolism", Radiology, Sep. 2005:236:3 852-858.

Kucher, N., "Catheter Interventions in Massive Pulmonary Embolism", Cardiology Rounds, Mar. 2006 vol. 10, Issue 3, 6 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of Chest Physicians 2008: 134:250-254.

Kuo, W. MD, "Endovascular Therapy for Acute Pulmonary Embolism", Continuing Medical Education Society of Interventional Radiology ("CME") Journal of Vascular and Interventional Radiology, Feb. 2012:23: 167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology, 2011: 34:106-113.

Muller-Hulsbeck, S. et al. "Mechanical Thrombectomy of Major and Massive Pulmonary Embolism with Use of the Amplatz Thrombectomy Device", Investigative Radiology Jun. 2001:36:6:317-322.

Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radio 116:7-10 1993, 4 pages.

Schmitz-Rode et al., "Temporary Pulmonary Stent Placement as Emergency Treatment of Pulmonary Embolism," Journal of the American College of Cardiology, vol. 48, No. 4, 2006, 5 pages.

Schmitz-Rode, T. et al., "Massive Pulmonary Embolism: Percutaneous Emergency Treatment by Pictail Rotation Catheter", JACC Journal of the American College of Cardiology, Aug. 2000:36:2:375-380.

Tapson, V., "Acute Pulmonary Embolism", The New England Journal of Medicine, Mar. 6, 2008:358:2037-52.

Truong et al., "Mechanical Thrombectomy of Iliocaval Thrombosis Using a Protective Expandable Sheath," Cardiovasc Intervent Radio! 27-254-258, 2004, 5 pages.

Turk et al., "ADAPT FAST study: a direct aspiration first pass technique for acute stroke thrombectomy." J Neuro Intervent Surg, vol. 6, 2014, 6 pages.

Uflacker, R., "Interventional Therapy for Pulmonary Embolism", Journal of Vascular and Interventional Radiology Feb. 2001: 12:147-164.

Verma, R., MD et al. "Evaluation of a Newly Developed Percutaneous Thrombectomy Basket Device in Sheep With Central Pulmonary Embolisms", Investigative Radiology, Oct. 2006, 41, 729-734.

U.S. Appl. No. 15/466,740, filed Mar. 22, 2017.
U.S. Appl. No. 15/498,320, filed Apr. 26, 2017.

\* cited by examiner

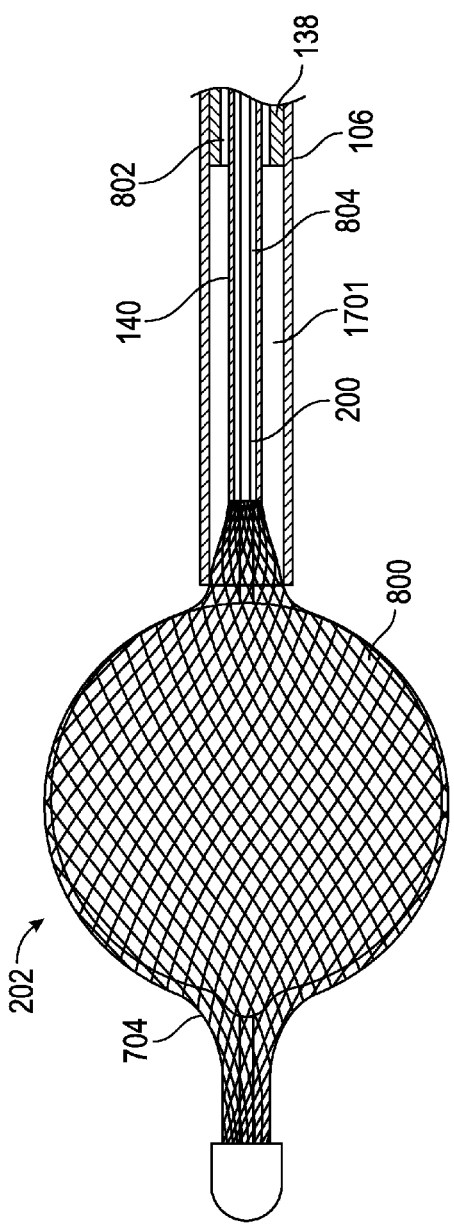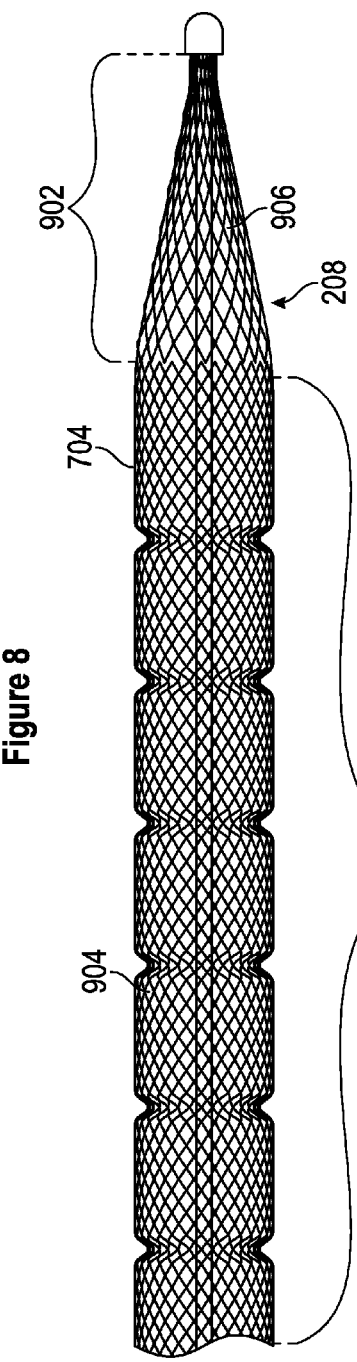

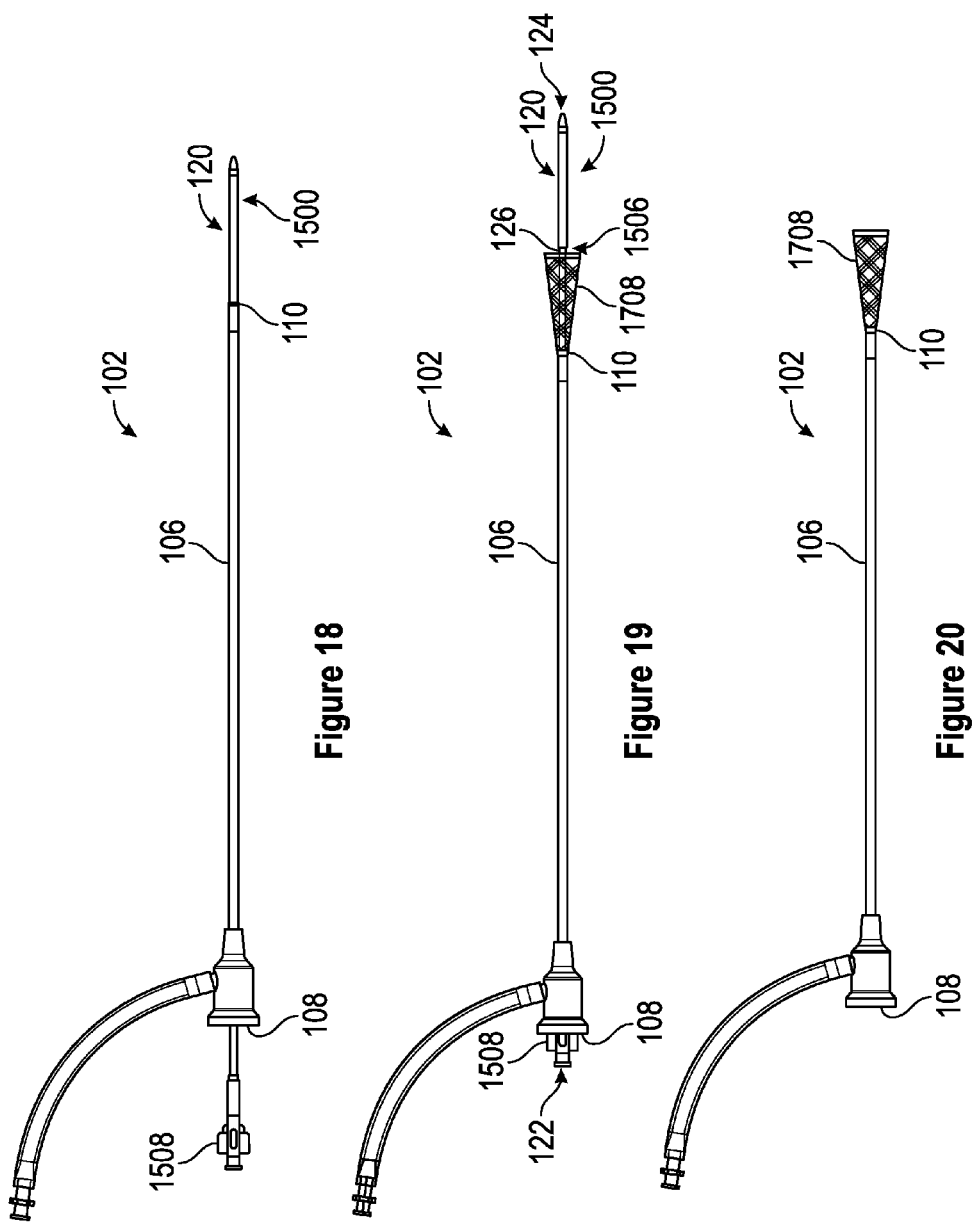

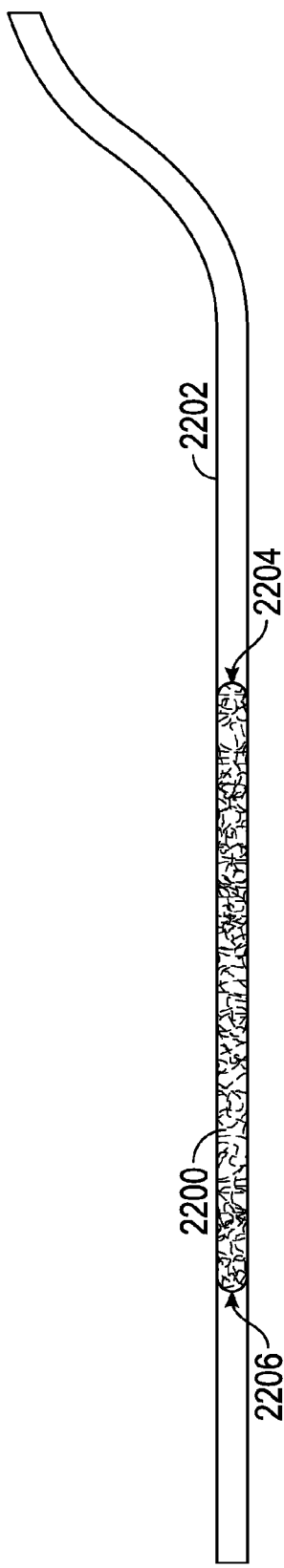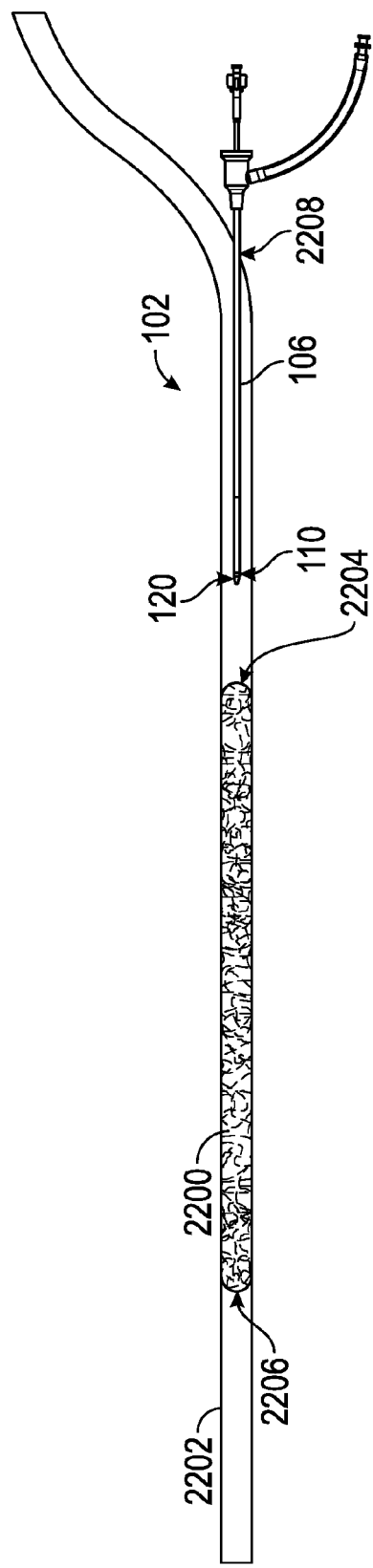
Figure 23-A
Figure 23-B

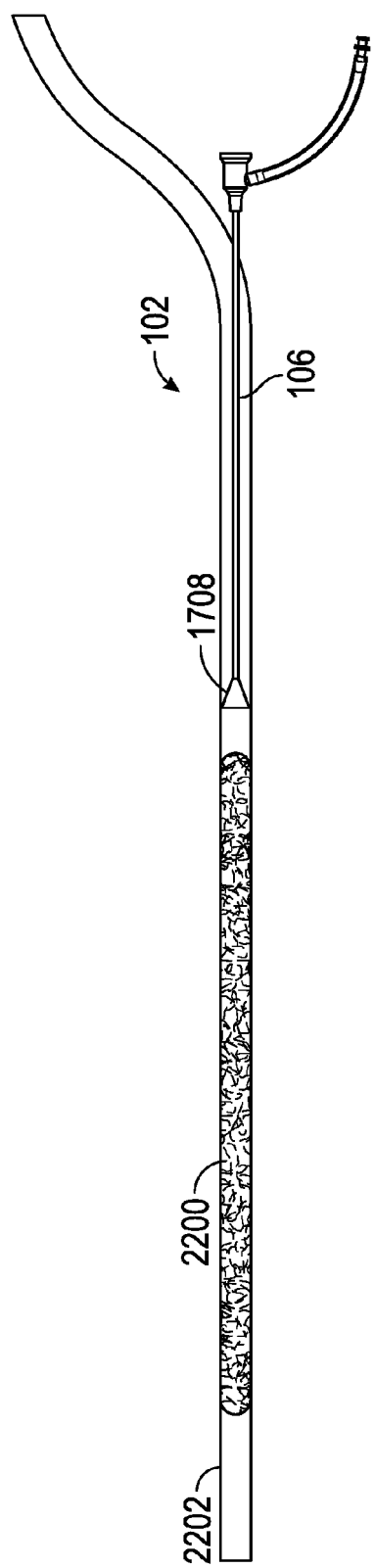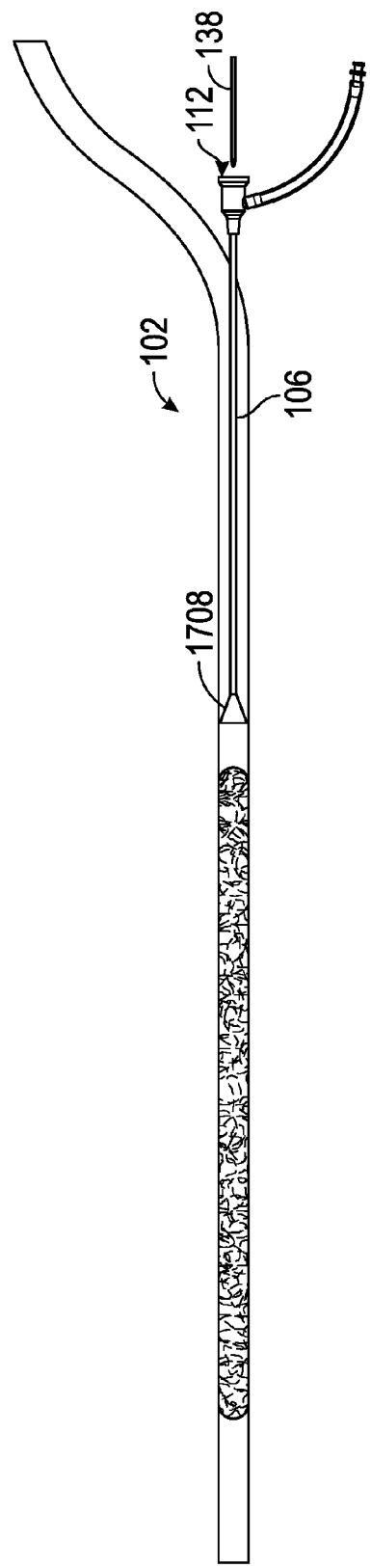
Figure 23-C
Figure 23-D

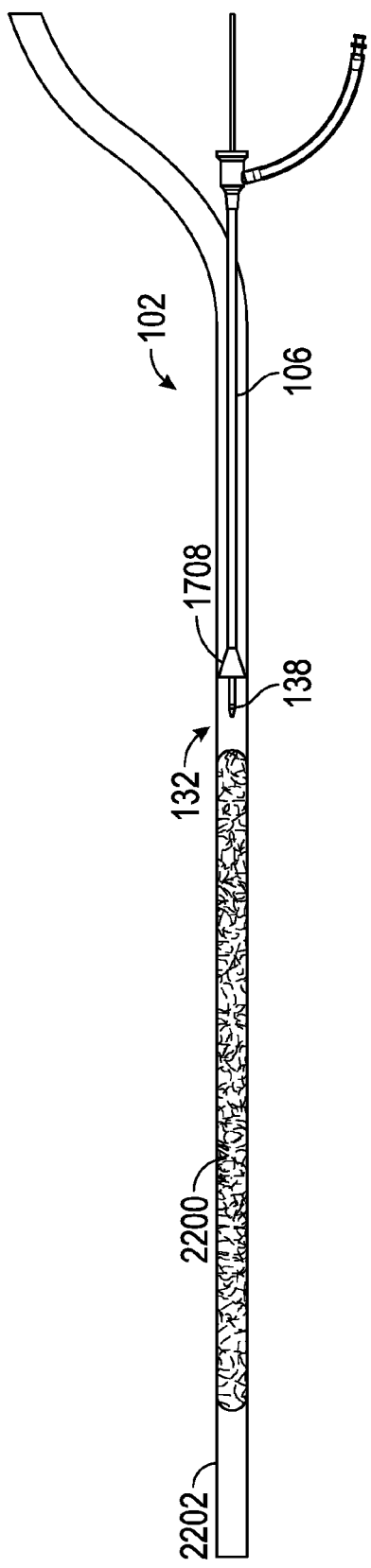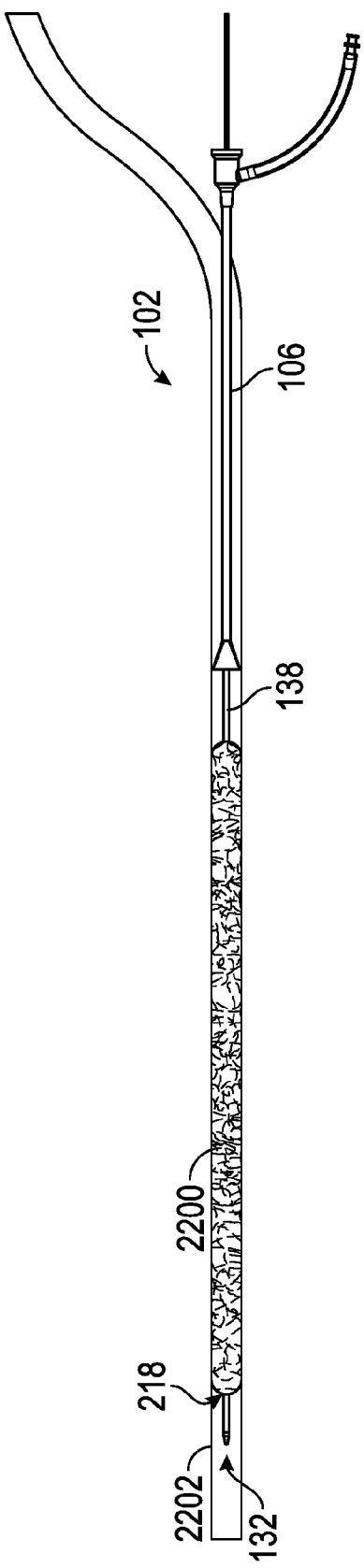
Figure 23-E
Figure 23-F

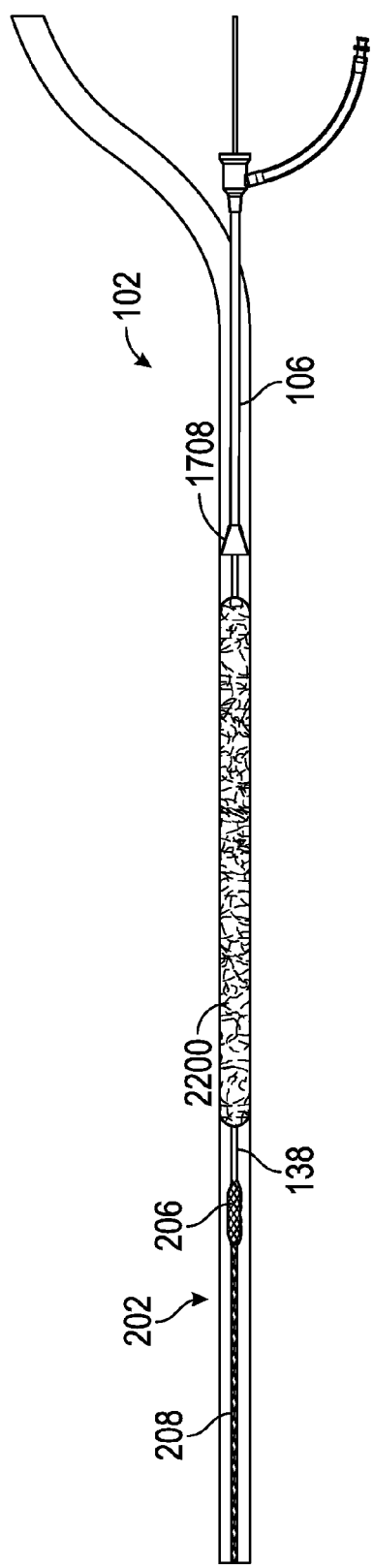
Figure 23-G
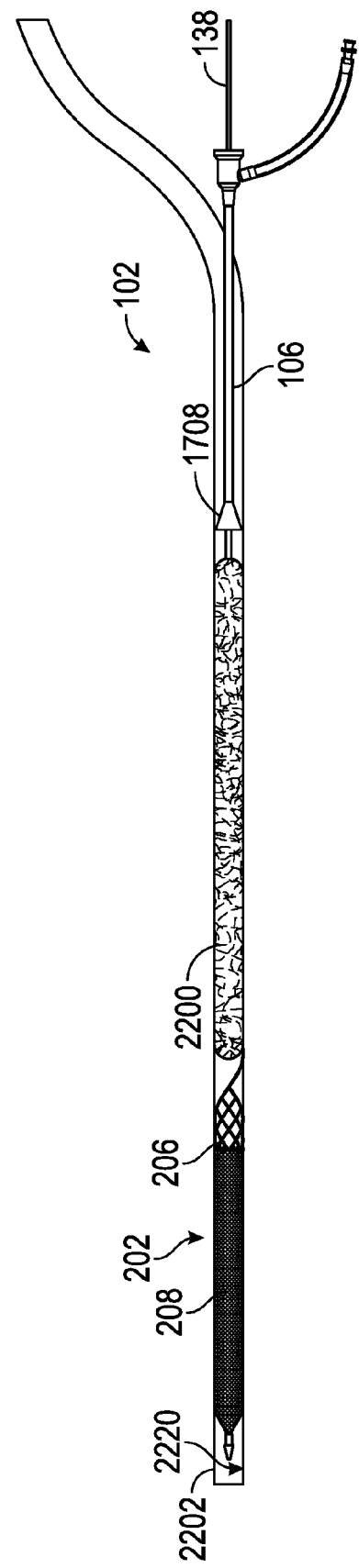
Figure 23-H

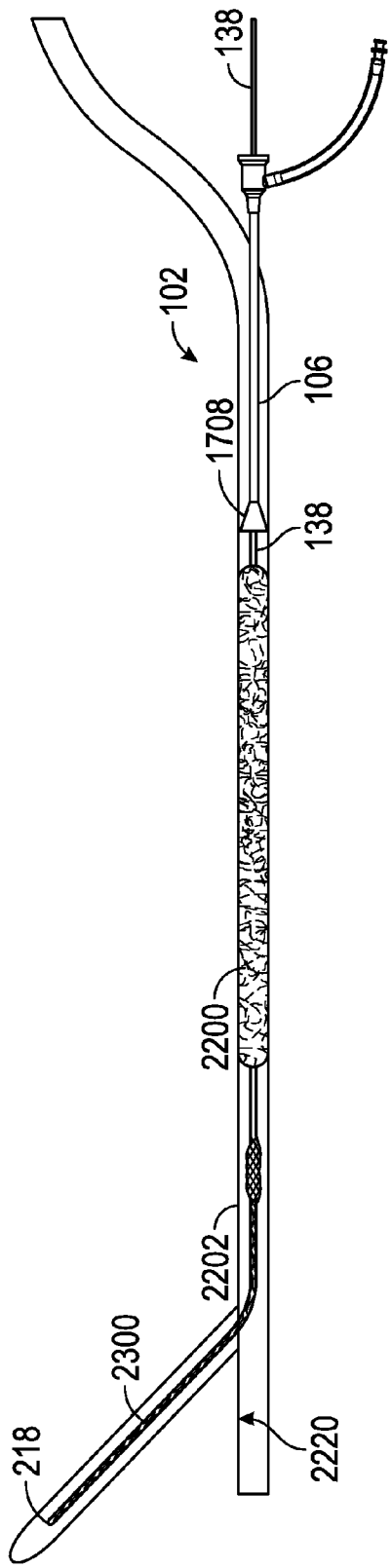
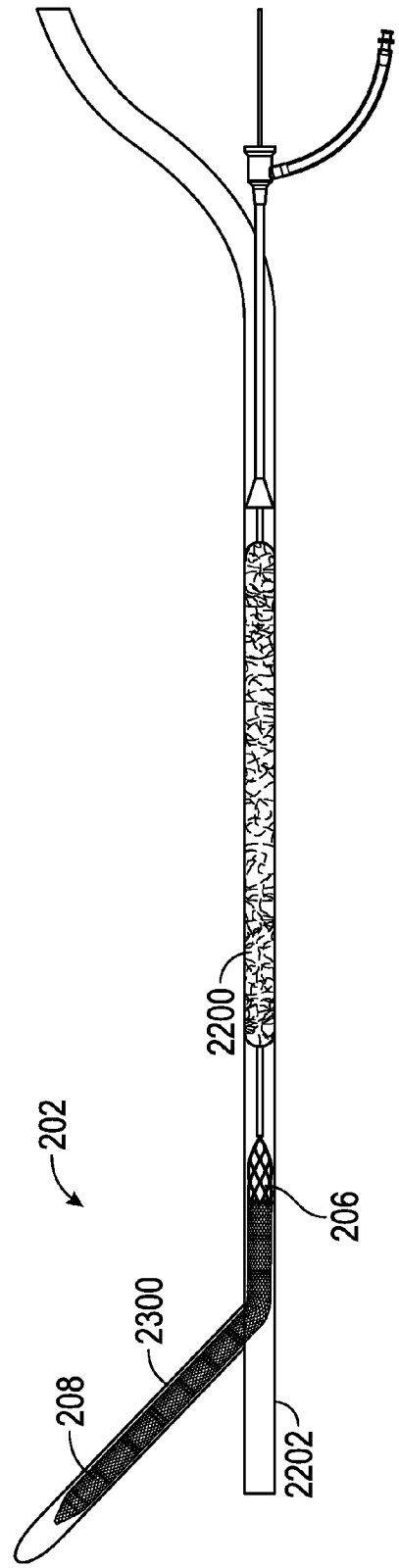
Figure 24-A
Figure 24-B

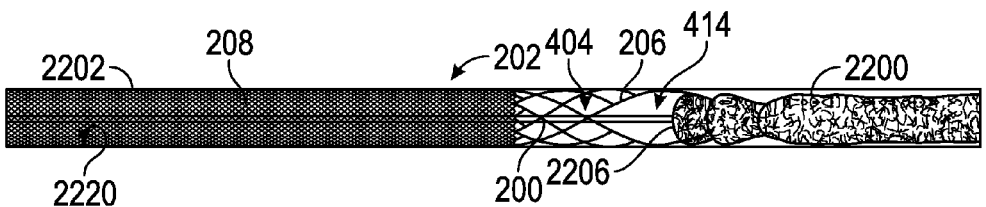
Figure 25-A
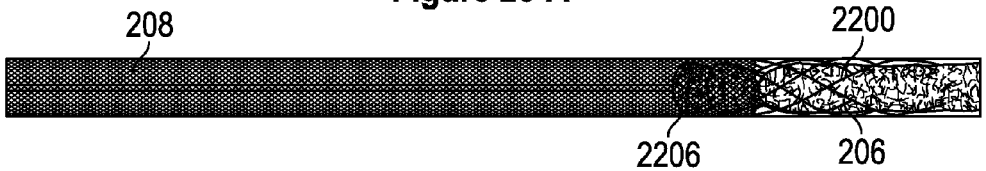
Figure 25-B
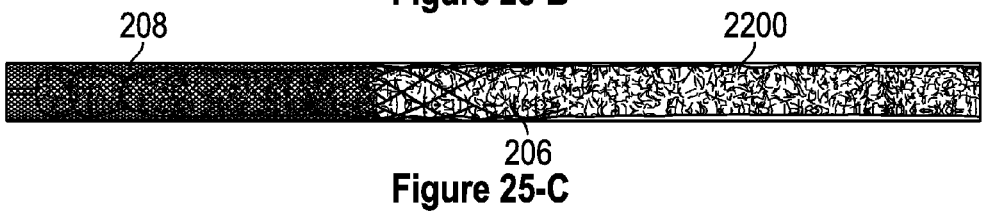
Figure 25-C
Figure 25-D
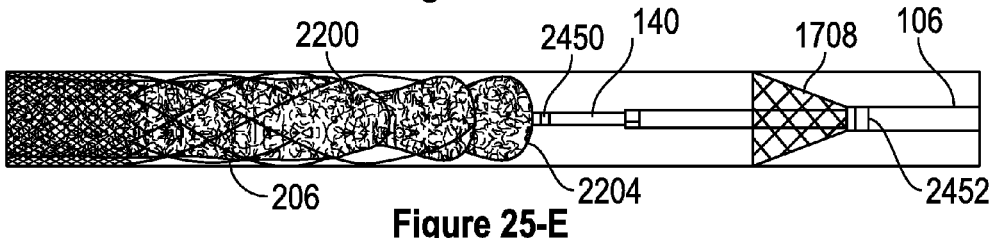
Figure 25-E
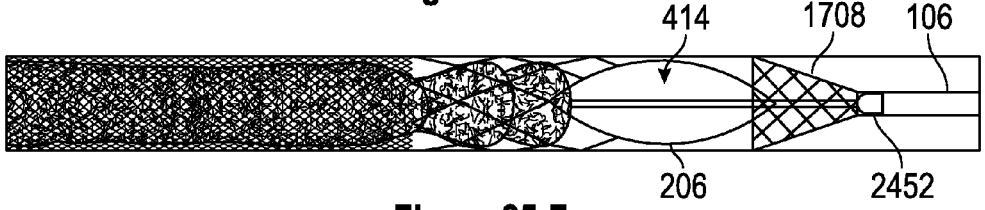
Figure 25-F
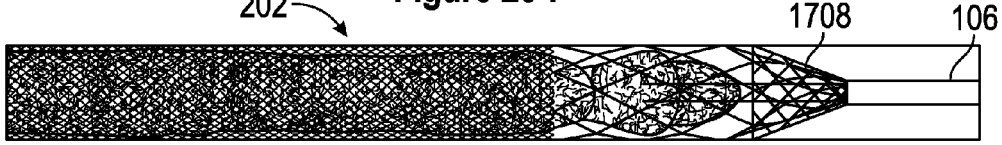
Figure 25-G
Figure 25-H

INTRAVASCULAR TREATMENT OF VASCULAR OCCLUSION AND ASSOCIATED DEVICES, SYSTEMS, AND METHODS

CROSS-REFERENCES TO RELATED APPLICATIONS

This application is a continuation of U.S. application Ser. No. 15/268,296, filed on Sep. 16, 2016, and entitled "INTRAVASCULAR TREATMENT OF VASCULAR OCCLUSION AND ASSOCIATED DEVICES, SYSTEMS, AND METHODS", which claims the benefit of U.S. Provisional Application No. 62/245,935, filed on Oct. 23, 2015, and entitled "INTRAVASCULAR TREATMENT OF VASCULAR OCCLUSION AND ASSOCIATED DEVICES, SYSTEMS AND METHODS", the entirety of each of which are hereby incorporated by reference herein.

BACKGROUND OF THE INVENTION

Thrombosis is a term for a blood clot occurring inside a blood vessel, and a venous thrombus is a blood clot (thrombus) that forms within a vein. A common type of venous thrombosis is a deep vein thrombosis (DVT). DVT is the formation of a blood clot (thrombus) within a deep vein, predominantly in the legs. Nonspecific signs may include pain, swelling, redness, warmness, and engorged superficial veins.

If the thrombus breaks off (embolizes) and flows towards the lungs, it can become a life-threatening pulmonary embolism (PE), a blood clot in the lungs. In addition to the loss of life that can arise from PE, DVT can cause significant health issues such as post thrombotic syndrome, which can cause chronic swelling, pressure, pain, and ulcers due to valve and vessel damage. Further, DVT can result in significant health-care costs either directly or indirectly through the treatment of related complications and inability of patients to work.

Three processes are believed to result in venous thrombosis. These are a decreased blood flow rate (venous stasis), increased tendency to clot (hypercoagulability), and changes to the blood vessel wall. DVT formation typically begins inside the valves of the calf veins, where the blood is relatively oxygen deprived, which activates certain biochemical pathways. Several medical conditions increase the risk for DVT, including diabetes, cancer, trauma, and antiphospholipid syndrome. Other risk factors include older age, surgery, immobilization (as with bed rest, orthopedic casts, and sitting on long flights), combined oral contraceptives, pregnancy, the postnatal period, and genetic factors. The rate of DVT increases dramatically from childhood to old age and in adulthood, about 1 in 1,000 adults develops it annually.

While current devices and methods of prevention and/or treatment of DVT exist, there are a number of shortcomings that have yet to be resolved, such as high incidence of DVT reoccurrence, use of devices not designed to remove large clot volumes, and/or complicated treatments involving multiple treatment devices and/or pharmaceuticals. Accordingly, new devices, systems, and methods of treating thrombus, and particularly DVT are desired.

BRIEF SUMMARY OF THE INVENTION

Aspects of the present disclosure relate to systems and methods for thrombus extraction, and particularly for thrombus extraction from a peripheral vasculature. The thrombus extraction devices of the present invention are designed to remove large clot volumes, including mature and organized clots, with reduced needs for pharmaceuticals, such as thrombolytics. This reduces risk of bleeding, post-treatment recovery time, and reduces health care procedure costs. The thrombus extraction device may comprise a self-expanding coring portion connected to a braided net so as to effectively core and separate large volumes of thrombus from large vessels in, for example, the venous system or arterial system while capturing the separated thrombus in the braided net.

In some embodiments, the thrombus can be extracted via the use of a thrombectomy system including an introducer sheath having a self-expanding funnel and a thrombus extraction catheter including a thrombus extraction device. The thrombus extraction device can include a self-expanding coring portion that can be a stent portion and an expandable cylindrical portion that can be a braided filament mesh. The expandable cylindrical portion can be formed onto a distal end of the self-expanding coring portion so as to form a unitary thrombus extraction device. In some embodiments, the coring element may have a sharp cutting edge to further enhance its ability to detach thrombus from the vessel wall.

One aspect of the present disclosure relates to a method of treating deep vein thrombosis in a peripheral vasculature of a patient. The method includes providing a thrombus extraction device including a proximal self-expanding coring portion, which can be a stent, formed of a unitary fenestrated structure and a distal expandable cylindrical portion, that can be tubular, formed of a braided filament mesh structure. In some embodiments, the mesh structure is integrally formed with the fenestrated structure so that a proximal end of the mesh structure is attached to a distal end of the fenestrated structure. The method includes advancing a catheter constraining the thrombus extraction device through a vascular thrombus in a venous vessel. In some embodiments, an intermediate shaft slidably extends through the catheter and a distal end thereof is coupled to a proximal end of the fenestrated structure. In some embodiments, an inner shaft slidably extends through the intermediate shaft and a distal end thereof is coupled to a distal end of the mesh structure. The method includes deploying the thrombus extraction device from the catheter from a constrained configuration to an expanded configuration. In some embodiments, the thrombus extraction device engages at least a wall of the venous vessel distally past a portion of the vascular thrombus at full expansion. The method includes retracting the thrombus extraction device proximally so that the coring portion cores and separates a portion of the vascular thrombus from the venous vessel wall while the mesh structure captures the vascular thrombus portion. The method includes withdrawing the thrombus extraction device from the patient to remove the vascular thrombus portion from the venous vessel.

In some embodiments, advancing the catheter includes inserting the catheter into the venous vessel until a radiopaque distal tip of the catheter is distally past the vascular thrombus portion. In some embodiments, deploying the thrombus extraction device from the catheter from the constrained configuration to the expanded configuration includes advancing the intermediate shaft distally until the coring portion of the thrombus extraction device is beyond a distal end of the catheter.

In some embodiments, deploying the thrombus extraction device further includes: locking the intermediate shaft with respect to the catheter; retracting the inner shaft with respect to the catheter and the intermediate shaft until a stop feature fixed on the inner shaft engages a corresponding feature on the stent portion slidably connected to the inner shaft for full expansion of the thrombus extraction device, which stent portion maintains sufficient radial force on the venous vessel wall to core and separate the vascular thrombus portion at full expansion; and dynamically coupling the inner shaft with respect to the intermediate shaft. In some embodiments, the coring portion has a coring angle between 30 degrees and 45 degrees when the thrombus extraction device is at full expansion. In some embodiments, deploying the thrombus extraction device further includes determining a position of the thrombus extraction device with respect to the catheter via imaging of a first radiopaque marker located on the catheter and a second radiopaque marker located on at least one of the intermediate shaft, the inner shaft, stent portion, or mesh structure.

In some embodiments, the vascular thrombus portion is captured into the mesh structure by entering the expandable tubular portion and/or cylindrical portion via at least opening or aperture located at the proximal end of the self-expanding stent portion. In some embodiments, the method includes inserting the catheter into the venous vessel through an access site, which access site is a popliteal access site, a femoral access site, or an internal jugular access site. In some embodiments, the venous vessel has a diameter of at least 5 millimeters and is at least one of a femoral vein, an iliac vein, a popliteal vein, a posterior tibial vein, an anterior tibial vein, or a peroneal vein.

In some embodiments the method further includes: percutaneously accessing the venous vessel of the patient with an introducer sheath through an access site into the venous vessel of the patient; advancing a distal end of the introducer sheath to a position proximal of the vascular thrombus; deploying a self-expanding funnel on the distal end of the introducer sheath; and inserting the catheter through a lumen of the introducer sheath so that a distal tip of the catheter is distally past the vascular thrombus portion. In some embodiments, deploying the self-expanding funnel includes: advancing an obturator having a capture sheath feature on a distal end thereof to unsheathe the self-expanding funnel from a constrained configuration within the capture sheath feature to a deployed configuration free of the capture sheath feature; and removing the obturator from the introducer sheath by retracting the obturator through or outside the deployed self-expanding funnel and through or outside the lumen of the introducer sheath. In some embodiments, withdrawing the thrombus extraction device from the patient includes: retracting the thrombus extraction device relative to the introducer sheath until an opening of the self-expanding stent portion is within the self-expanding funnel; collapsing the stent portion and mesh structure so as to compress the vascular thrombus portion therein; retracting the stent portion and mesh structure into the introducer sheath; and removing the thrombus extraction device from the introducer sheath.

In some embodiments the method further includes extruding at least some of the vascular thrombus portion through pores located at a distal portion of the expandable tubular portion and/or cylindrical portion and capturing a part of the at least some of the vascular thrombus portion in the self-expanding funnel or further compressing the at least one piece of the vascular thrombus portion through a mesh of the self-expanding funnel. In some embodiments the method further includes aspirating at least one piece of the vascular thrombus portion remaining within the self-expanding funnel from the venous vessel and through an aspiration port connected to a proximal end of the introducer sheath.

In some embodiments the method further includes verifying that the opening of the self-expanding stent portion is within the self-expanding funnel via fluoroscopy prior to collapsing the stent portion and mesh structure. In some embodiments, collapsing the stent portion and mesh structure includes: decoupling the inner shaft and the intermediate shaft; and advancing the inner shaft distally relative to the intermediate shaft. In some embodiments the method includes aspirating or infusing a thrombolytic agent into or from the venous vessel before, during, or after thrombus extraction.

One aspect of the present disclosure relates to a method of treating deep vein thrombosis in a peripheral vasculature of a patient. The method includes: percutaneously accessing a venous vessel of a patient with an introducer sheath through a popliteal access site into the venous vessel of the patient; and inserting a catheter constraining a thrombus extraction device through a lumen of the introducer sheath so that a distal tip of the catheter is distally past a portion of the vascular thrombus in the venous vessel, which thrombus extraction device includes a proximal self-expanding stent portion formed of a unitary fenestrated structure and a distal expandable tubular portion and/or cylindrical portion formed of a braided filament mesh structure. In some embodiments, a proximal end of the mesh structure is attached to a distal end of the fenestrated structure. The method includes deploying the thrombus extraction device from the catheter from a constrained configuration to an expanded configuration by advancing an intermediate shaft distally until the stent portion of the thrombus extraction device is beyond a distal end of the catheter, which intermediate shaft slidably extends through the catheter and a distal end thereof is coupled to a proximal end of the fenestrated structure. The method includes retracting the thrombus extraction device proximally so that the stent portion cores and separates a portion of the vascular thrombus from the venous vessel wall while the mesh structure captures the vascular thrombus portion. The method includes withdrawing the thrombus extraction device from the patient.

In some embodiments, deploying the thrombus extraction device further includes retracting an inner shaft with respect to the catheter and the intermediate shaft until a stop feature on the inner shaft engages a corresponding feature on the stent portion for full expansion of the thrombus extraction device. In some embodiments, the stent portion maintains sufficient radial force on the venous vessel wall to core and separate the vascular thrombus portion at full expansion, and in some embodiments the inner shaft slidably extends through the intermediate shaft and a distal end thereof is coupled to a distal end of the mesh structure. In some embodiments the method includes deploying a self-expanding funnel on a distal end of the introducer sheath proximal of the vascular thrombus. In some embodiments, deploying the self-expanding funnel includes: advancing an obturator having a capture sheath feature on a distal end thereof to unsheathe the self-expanding funnel from a constrained configuration within the capture sheath feature to a deployed configuration free of the capture sheath feature; and removing the obturator from the introducer sheath by retracting the obturator through or outside the deployed self-expanding funnel and through or outside the lumen of the introducer sheath.

One aspect of the present disclosure relates to a method for removal of thrombus from a blood vessel in a body of a patient, which blood vessel can be an artery or a vein. The method includes: providing a thrombus extraction device including a proximal self-expanding member formed of a unitary fenestrated structure, a distal substantially cylindrical portion formed of a net-like filament mesh structure which is attached to the unitary fenestrated structure, and an inner shaft member connected to a distal end of the net-like filament mesh structure; advancing a catheter constraining the thrombus extraction device through a vascular thrombus, and deploying the thrombus extraction device by either advancing the thrombus extraction device beyond a distal end of the catheter or retracting the catheter relative to the thrombus extraction device, thus exposing the thrombus extraction device distally past a portion of the thrombus and allowing expansion of the thrombus extraction device to engage a wall of the blood vessel. The method includes: retracting the thrombus extraction device to separate a portion of the thrombus from the vessel wall and to capture the portion of the thrombus within the net-like filament mesh structure; and withdrawing the thrombus extraction device from the body to remove thrombus from the patient.

In some embodiments, advancing the catheter includes inserting the catheter into the blood vessel until a radiopaque distal tip of the catheter is distally past the thrombus portion. In some embodiments, the net-like filament mesh structure is integrally formed with the fenestrated structure so that a proximal end of the net-like filament mesh structure is attached to a distal end of the fenestrated structure. In some embodiments, the self-expanding member of the thrombus extraction device includes a stent portion, which retracting the thrombus extraction device further includes coring the thrombus portion from the vessel wall with the stent portion. In some embodiments, the thrombus portion is captured with the net-like filament mesh structure by entering the net-like filament mesh structure via at least one aperture or opening located at a proximal end of the stent portion.

In some embodiments, the thrombus extraction device is advanced beyond the distal end of the catheter by advancing an intermediate shaft distally through the catheter, which intermediate shaft slidably extends through the catheter and a distal end of the intermediate shaft is coupled to a proximal end of the fenestrated structure. In some embodiments the method includes, retracting the inner shaft member relative to the catheter and the intermediate shaft until a stop feature fixed on the inner shaft member engages a corresponding feature on the fenestrated structure and locking the inner shaft member with respect to the intermediate shaft for full expansion of the thrombus extraction device. In some embodiments, the inner shaft member can be dynamically locked with respect to the intermediate shaft.

In some embodiments the method includes, collapsing the thrombus extraction device so as to compress the thrombus portion therein prior to withdrawing the thrombus extraction device from the body. In some embodiments, collapsing includes unlocking the inner shaft member and the intermediate shaft and advancing the inner shaft member distally relative to the intermediate shaft.

In some embodiments the method includes, fluoroscopically monitoring deployment of the thrombus extraction device and ceasing advancing the thrombus extraction device beyond the distal end of the catheter or retracting the catheter relative to the thrombus extraction device based on a position of a first radiopaque marker located on the catheter relative to a second radiopaque marker located on the thrombus extraction device. In some embodiments, the thrombus is located in a peripheral vasculature of the patient and the blood vessel has a diameter of at least 5 millimeters and includes at least one of a femoral vein, an iliac vein, a popliteal vein, a posterior tibial vein, an anterior tibial vein, or a peroneal vein.

In some embodiments the method includes, percutaneously accessing a blood vessel that can be venous vessel of the patient with an introducer sheath through a popliteal access site and inserting the catheter through a lumen of the introducer sheath and into the venous vessel of the patient. In some embodiments the method includes, percutaneously accessing a venous vessel of the patient with an introducer sheath through a femoral access site and inserting the catheter through a lumen of the introducer sheath and into the venous vessel of the patient, which thrombus extraction device extends within a popliteal sheath and retraction of the thrombus of the extraction device is in a direction of blood flow. In some embodiments the method includes, percutaneously accessing a venous vessel of the patient with an introducer sheath through an internal jugular access site and inserting the catheter through a lumen of the introducer sheath and into the venous vessel of the patient, which thrombus extraction device extends within a popliteal sheath extending from the patient and retraction of the thrombus of the extraction device is in a direction of blood flow. In some embodiments the method includes, aspirating or infusing a thrombolytic agent into or from the blood vessel before, during, or after thrombus extraction.

One aspect of the present disclosure relates to a thrombus extraction device for removal of a vascular thrombus from a blood vessel of a patient. The thrombus extraction device includes: a catheter having a proximal end and a distal end, an outer shaft defining a first lumen, an intermediate shaft defining a second lumen, and an inner shaft, which intermediate shaft is coaxial the first lumen and the inner shaft is coaxial the second lumen; a proximal self-expanding coring element formed of a unitary fenestrated structure having a proximal end and a distal end and configured to core and separate a portion of the vascular thrombus from the blood vessel, which proximal end of the fenestrated structure is coupled to the distal end of the intermediate shaft; and a distal expandable cylindrical portion formed of a braided filament mesh structure having a proximal end and a distal end and configured to capture the vascular thrombus portion, which proximal end of the mesh structure is attached to the distal end of the fenestrated structure, and which distal end of the mesh structure is coupled to the distal end of the inner shaft. In some embodiments, full expansion of the mesh structure and fenestrated structure varies based on a position of the intermediate shaft relative the inner shaft of the catheter.

In some embodiments, the coring element includes a stent. In some embodiments, the stent includes a ring feature slidably coupled to the inner shaft and/or to one or several strut(s) of the stent and the inner shaft includes a stop feature fixed to the inner shaft, which stop feature is configured to engage with the ring feature when the mesh structure and the stent are in full expansion.

In some embodiments the device includes, a locking mechanism that can secure the inner shaft relative to the intermediate shaft when the mesh structure and the stent are in full expansion. In some embodiments, the locking mechanism can maintain a desired radial force on a vessel wall when the stent is compressed. In some embodiments, the locking mechanism moveably secures the inner shaft relative to the intermediate shaft via a spring.

In some embodiments, the proximal end of the mesh structure is integrally formed with the distal end of the fenestrated structure to create a unitary structure. In some embodiments, the coring element and the mesh structure are receivable within the outer shaft. In some embodiments, the coring element and mesh structure are in a constrained configuration when received within the outer shaft and an expanded configuration when free of the constraining outer shaft.

In some embodiments, the mesh structure includes a plurality of radial ribs or grooves longitudinally spaced between the proximal and distal ends of the mesh structure. In some embodiments, the mesh structure has a first pore size at a proximal portion and a second pore size at a distal portion, which first pore size is different from the second pore size. In some embodiments, the second pore size is greater than the first pore size.

In some embodiments, the proximal end of the fenestrated structure is coupled to the distal end of the intermediate shaft via a plurality of struts extending at a coring angle relative to a longitudinal axis of the thrombus extraction device. In some embodiments, the coring angle is in a range between 30 degrees and 45 degrees. In some embodiments, the coring element has a length in a range between 25 millimeters and 100 millimeters and the mesh structure has a length in a range between 100 millimeters and 500 millimeters in, for example, the collapsed state. In some embodiments, the coring element has a diameter in a range between 8 millimeters and 25 millimeters at full expansion and the mesh structure has a diameter in a range between 8 millimeters and 25 millimeters at full expansion.

In some embodiments, the fenestrated structure includes a plurality of interconnected struts. In some embodiments, the proximal end of the fenestrated structure has fewer struts than the distal end of the fenestrated structure to thereby facilitate collapse of the coring element and to facilitate maintenance of a coring orientation when the blood vessel is tortuous. In some embodiments, the fenestrated structure includes a plurality of interconnected struts defining an opening at the proximal end of the fenestrated structure. In some embodiments, at least some of the plurality of interconnected struts defining the opening include a sharpened proximal edge.

In some embodiments the device includes, a first radiopaque marker located on the outer shaft and a second radiopaque marker located on the distal end of the inner shaft. In some embodiments the device includes, a locking mechanism that can secure a relative position of the outer shaft with respect to the intermediate shaft. In some embodiments the device includes, a handle including a plunger that can control a relative position of the inner shaft with respect to the intermediate shaft and to selectively secure the relative position of the inner shaft with respect to the intermediate shaft.

One aspect of the present disclosure relates to an introducer sheath for accessing and removing thrombus within a blood vessel of a patient. The introducer sheath includes: an elongate sheath including a proximal end, a distal end, and a lumen extending therebetween; a self-expanding funnel affixed to the distal end of the elongate sheath; and an obturator including an elongate shaft having a capture sheath located proximate to a distal end of the obturator, which capture sheath can retain the self-expanding funnel in a constrained configuration and the obturator is configured to be received within the lumen of the elongate sheath.

In some embodiments the introducer sheath includes, a sealed hub located at the proximal end of the elongate sheath. In some embodiments, the sealed hub includes an aspiration port. In some embodiments, the self-expanding funnel has a diameter equal to or less than a diameter of the elongate sheath when the self-expanding funnel is in the constrained configuration. In some embodiments, the obturator includes an atraumatic tip located at the distal end of the obturator, which atraumatic tip is radiopaque. In some embodiments, the obturator includes a connection fitting configured to sealingly connect with the distal end of the elongate sheath. In some embodiments, the self-expanding funnel is permeable to blood. In some embodiments, the self-expanding funnel includes a conical shape formed from at least one of a castellated nitinol braid, a nitinol braided stent, a laser cut nitinol, a laser cut polymer tube, an injection molded polymeric structure, or an inflatable balloon.

One aspect of the present disclosure relates to a method of accessing and removing thrombus from a venous vessel of a patient. The method includes: providing an introducer sheath including an elongate sheath defining a lumen, a self-expanding funnel affixed to a distal end of the elongate sheath, and an elongate obturator extending through the lumen and retaining the self-expanding funnel in a constrained configuration within a capture sheath of the obturator; percutaneously accessing a venous vessel of a patient with the introducer sheath through an access site, which access site includes a popliteal access site, a femoral access site, or an internal jugular access site; advancing a distal end of the introducer sheath to a position proximal of a thrombus; deploying the self-expanding funnel from the constrained configuration within the capture sheath to an expanded configuration free of the capture sheath; capturing thrombus in the self-expanding funnel; and aspirating the captured material through the lumen of the elongate sheath.

In some embodiments, deploying the self-expanding funnel includes distally advancing the obturator relative to the elongate sheath to unsheathe the self-expanding funnel from the constrained configuration to the expanded configuration and removing the obturator from the introducer sheath by proximally retracting the obturator through the deployed self-expanding funnel and through the lumen of the elongate sheath. In some embodiments, deploying the self-expanding funnel includes proximally retracting the sheath over the obturator to unsheathe the self-expanding funnel from the constrained configuration to the expanded configuration and removing the obturator from the introducer sheath by proximally retracting the obturator through or outside of the deployed self-expanding funnel and through or outside of the lumen of the elongate sheath.

In some embodiments the method includes, inserting a catheter constraining a thrombus extraction device through the lumen of the elongate sheath so that a distal tip of the catheter is distally past the vascular thrombus portion, deploying the thrombus extraction device from the catheter, and proximally retracting the thrombus extraction device relative to the introducer sheath until an opening of the thrombus extraction device is within the self-expanding funnel. In some embodiments the method includes, extruding a portion of thrombus captured by the thrombus extraction device through the thrombus extraction device. In some embodiments, the thrombus captured by the self-expanding funnel includes the extruded portion of thrombus captured by the thrombus extraction device.

One aspect of the present disclosure relates to a thrombectomy system for removal of a vascular thrombus from a blood vessel of a patient. The thrombectomy system includes: a thrombus extraction catheter including a thrombus extraction device. The thrombus extraction devices includes: a proximal self-expanding coring element formed of a unitary fenestrated structure; and a distal expandable cylindrical portion formed of a braided filament mesh structure having a proximal end attached to a distal end of the fenestrated structure. The thrombectomy system includes: a catheter including a lumen constraining the thrombus extraction device, an intermediate shaft connected to a proximal end of the self-expanding coring element, and an inner shaft connected to a distal end of the expandable cylindrical portion and slidably displaceable with respect to the intermediate shaft to control expansion of the expandable cylindrical portion. The thrombectomy system includes: an introducer sheath including: an elongate sheath defining an insertion lumen; a self-expanding funnel affixed to a distal end of the elongate sheath; and an elongate obturator including a sheath capture feature configured to retain the self-expanding funnel in a constrained configuration.

In some embodiments, the obturator is configured to be received within the lumen of the elongate sheath and includes a connection fitting configured to sealingly connect with a distal end of the elongate sheath. In some embodiments, the self-expanding funnel has a length that is at least equal to a length of the self-expanding coring element. In some embodiments, the introducer sheath includes a self-sealing aperture located at a proximal end of the introducer sheath.

In some embodiments the thrombectomy system includes, an aperture dilator sized to be receivable within the self-sealing aperture and having an internal diameter larger than a diameter of the self-sealing aperture in a sealed configuration. In some embodiments, the introducer sheath includes an aspiration port located at a proximal end of the inserter sheath, which aspiration port is selectably fluidly connected to the insertion lumen via an aspiration valve.

In some embodiments, the insertion lumen is sized to slidably receive the thrombus extraction catheter. In some embodiments, the expandable cylindrical portion is formed on the self-expanding coring element to form a unitary thrombus extraction device.

One aspect of the present disclosure relates to a method of manufacturing a unitary thrombus extraction device including a proximal fenestrated structure including a plurality of struts and a distal net-like filament mesh structure formed on a distal end of the fenestrated structure. The method includes: identifying a plurality of formation points formed by some of the plurality of struts of the unitary fenestrated structure; threading a unique pair of wires including a first wire and a second wire overlaying the first wire through each of the formation points; and weaving the net-like filament mesh structure from the unique pairs of wires such that one of: the first wires and the second wires do not form loops about the formation points through which the first wires and second wires are threaded, and such that the other of: the first wires and the second wires form loops about the formation points through which the first wires and the second wires are threaded.

In some embodiments, the net-like filament mesh structure is woven from the unique pairs of wires such that the first wires do not form loops about the formation points through which the first wires are threaded and such that the second wires form loops about the formation points through which the second wires are threaded. In some embodiments, each of the formation points includes a peak strut. In some embodiments, the fenestrated structure includes 12 peak struts. In some embodiments, the net-like filament mesh includes 48 wires. In some embodiments, the net-like filament mesh structure is manually woven. In some embodiments, the net-like filament mesh structure is automatically woven.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 8 is a view of one embodiment of a ball shaped thrombus captured in a thrombus extraction device.

FIG. 9 is a side view of one embodiment of the braided filament mesh structure having multiple pore sizes.

FIG. 18 is a side view of one embodiment of an introducer sheath in an undeployed configuration.

FIG. 19 is a side view of one embodiment of an introducer sheath in a partially deployed configuration.

FIG. 20 is a side view of one embodiment of an introducer sheath in a deployed configuration.

FIGS. 23-A through 23-H are views depicting one embodiment of a process for fully expanding the thrombus extraction device in a blood vessel.

FIGS. 24-A and 24-B are views depicting alternative steps in the process for fully expanding the thrombus extraction device in a blood vessel.

FIGS. 25-A through 25-H are views depicting one embodiment of a process for removal of thrombus with an expanded thrombus extraction device.

DETAILED DESCRIPTION OF THE INVENTION

Figure 1:
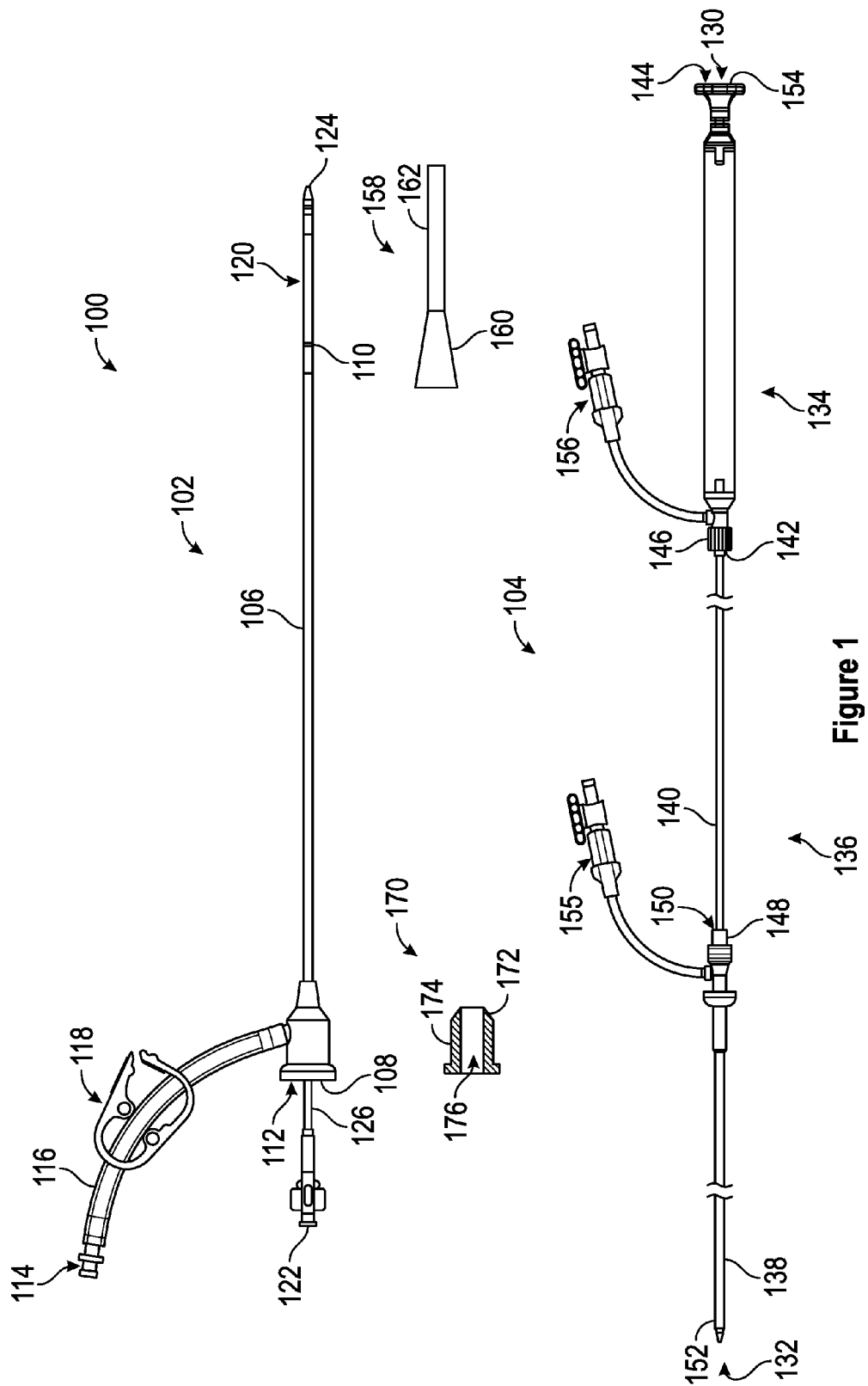
FIG. 1 is a perspective view of one embodiment of a thrombectomy system for removal of a thrombus from a blood vessel of a patient.

The present disclosure relates to a thrombectomy system for removal of a vascular thrombus from a blood vessel of a patient. The thrombectomy system can remove thrombus from a blood vessel, and particularly from a venous vessel of a patient via the coring of the thrombus and/or the separating of the thrombus from the walls of the blood vessel that can occur when the thrombectomy system is retracted through the vascular thrombus. Thrombus that is cored and/or separated from the walls of the blood vessel can be captured within the thrombectomy system and removed from the patient.

The thrombectomy system can include a thrombus extraction catheter including a Thrombus Extraction Device ("TED"). The TED can include a proximal self-expanding coring element that can be a stent portion and/or that can be formed of a unitary fenestrated structure. The TED can include a distal expandable cylindrical portion formed of a braided filament mesh structure. The braided filament mesh structure can be formed on the coring element to thereby form a unitary TED. This forming of the braided filament mesh structure directly on the coring element can eliminate problems, such as: inconsistent material properties, decreased flexibility, decreased strength, and/or quality control issues, arising from connecting the braided filament mesh structure to the coring element via, for example, welding or adhesive.

The expansion of the TED can be controlled by the relative movement of portions of the thrombus extraction catheter. For example, a proximal end of the TED, and specifically a proximal end of the self-expanding coring element can be connected to an intermediate shaft that is slidable within an outer shaft of the thrombus extraction catheter. A distal end of the TED, and specifically a distal end of the expandable cylindrical portion can be connected to an inner shaft that is slidable within the intermediate shaft of the thrombus extraction catheter. As the inner shaft and the intermediate shaft are slidable with respect to the outer shaft, the TED can be withdrawn into the outer shaft to constrain the TED to an undeployed configuration, also referred to herein as a constrained configuration. Similarly, the TED can be deployed from the outer shaft by the relative movement of the intermediate shaft with respect to the outer shaft. After the TED has been deployed from the outer shaft, the inner shaft and the intermediate shaft can be moved with respect to each other to either expand or contract the expandable cylindrical portion of the TED and to bring the self-expanding coring element to full expansion.

The thrombectomy system can include an introducer sheath that can be sized to slidably receive the outer sheath of the thrombus extraction catheter. The introducer sheath can include a sealed aperture at a proximal end of the introducer sheath and a self-expanding funnel. The self-expanding funnel can be located at a distal end of the introducer sheath and can be selectably held in a constrained position by a capture sheath. In some embodiments, the self-expanding funnel can be slidably contained within the introducer sheath and can specifically be slidable with respect to the distal end of the introducer sheath. In some embodiments, the self-expanding funnel can be distally slide from a constrained configuration within the introducer sheath to a deployed configuration at which the self-expanding funnel extends from the distal end of the capture sheath.

The self-expanding funnel can be sized to engage with the self-expanding coring element when the TED is retracted towards the funnel. As the TED is retracted into the funnel, the funnel compresses the TED, and specifically the coring element, and guides the TED, and specifically the coring element into a lumen defined by the introducer sheath. The TED can be retracted until it is completely contained within the introducer sheath, and then the TED and the thrombus captured in the TED can be removed from the patient via the sealed aperture.

The thrombectomy system can access the blood vessel containing the thrombus via a plurality of access sites. These can include, for example, an internal jugular (IJ) access site, a femoral access site, a popliteal access site, or other venous or arterial access sites. The thrombectomy system can be used to extract thrombus and/or embolus from a variety of venous and/or arterial vessels, which can be peripheral vessels, including any vessel, including, by way of non-limiting example, a venous vessel, having a diameter of at least 5 millimeters (mm). The thrombectomy system can be inserted through an access point into a circulatory system of a patient and can be advanced to a position proximate to the thrombus. The TED can then be advanced through the thrombus, and, after being expanded distally of the thrombus, the TED can be retracted through the thrombus, thereby capturing all or portions of the thrombus.

With reference now to FIG. 1, one embodiment of a thrombectomy system 100, also referred to herein as a thrombus extraction system 100, is shown. The thrombectomy system 100 can be used to access a portion of a blood vessel such as a venous vessel containing thrombus and the thrombectomy system 100 can be used to remove all or portions of that thrombus from the blood vessel. The thrombectomy system 100 can include an introducer sheath 102 and a thrombus extraction catheter 104.

The introducer sheath 102 comprises an elongate member 106, also referred to herein as an elongate sheath 106, having a proximal end 108 and a distal end 110. The elongate member 106 can be elastic and/or flexible. The elongate member 106 can comprise any desired length and any desired diameter. In some embodiments, the elongate sheath 106 can have an outer diameter of at least 10 French, at least 12 French, at least 14 French, at least 18 French, at least 20 French, at least 22 French, between 14 French and 24 French, between 15 French and 21 French, between 16 French and 22 French, and/or any other or intermediate size.

The elongate member 106 can comprise a radiopaque marker that can be, for example, part of the distal end 110 of the elongate member 106. The elongate member 106 defines a lumen extending between the proximal end 108 and the distal end 110. The lumen 1701 (shown in FIG. 17) of the elongate member 106 can be sized to slidably receive the thrombus extraction catheter 104. In some embodiments, the lumen 1701 of the elongate member 106 can have an internal diameter of at least 2 French, at least 10 French, at least 14 French, at least 18 French, at least 20 French, at least 22 French, between 11 French and 12 French, between 10

French and 22 French, between 14 French and 21 French, between 16 French and 20 French, and/or any other or intermediate size. The lumen 1701 can terminate at a sealed aperture 112, also referred to herein as a sealed hub 112, located at the proximal end 108 of the elongate member 106. In some embodiments, the sealed aperture 112 can be self-sealing and/or can comprise a self-sealing seal.

The introducer sheath 102 can further include an aspiration port 114 that can be at the proximal end 108 of the elongate member 106 and/or connected to the proximal end 108 of the elongate member 106 via, for example, a connecting tube 116. In some embodiments, the aspiration port 114 can be a part of, and/or connected to the sealed hub 112. In some embodiments, the aspiration port 114 can be selectively fluidly connected to the lumen 1701 via, for example, a valve 118, also referred to herein as an aspiration valve 118, which valve 118 can be a tubing clamp that can be located at a position along the connecting tube 116 between the lumen 1701 and the aspiration port 114.

The introducer sheath 102 can further hold an obturator 120, also referred to herein as a dilator 120. The obturator 120 can be configured to hold a self-expanding funnel that can be attached to the distal end 110 of the elongate member 106 in a constrained configuration, and to release the self-expanding funnel from that constrained configuration. The obturator 120 can comprise a proximal end 122, a distal end 124, and an elongate shaft 126 extending therebetween. In some embodiments, the elongate shaft 126 can have a length that is greater than a length of the elongate member 106 of the introducer sheath 102. The obturator 120 can further define a lumen extending through the obturator 120, which lumen can receive a guidewire. In some embodiments, the guidewire can comprise any desired dimensions and can, in some embodiments, have a diameter of approximately 0.035 inches. The obturator 120 can be sized and shaped so as to be able to slidably move through the lumen of the elongate member 106.

The thrombectomy system 100 can include the thrombus extraction catheter 104. The thrombus extraction catheter 104 can have a proximal end 130 and a distal end 132. A handle 134, also referred to herein as a deployment handle 134, can be located at the proximal end 130 of the thrombus extraction catheter 104 and can connect to a catheter portion 136, also referred to herein as the catheter 136.

The catheter 136 can include an outer shaft 138, an intermediate shaft 140, and an inner shaft. The outer shaft 138 can comprise a variety of lengths and sizes. In some embodiments, the outer shaft 138 can be sized to slidably fit within the introducer sheath 102. In some embodiments, the outer shaft 138 can have a size of at least 8 French, at least 10 French, at least 11 French, at least 12 French, at least 14 French, at least 16 French, between 8 French and 14 French, between 11 French and 12 French, and/or any other or intermediate size.

Each of the outer shaft 138, the intermediate shaft 140, and the inner shaft can define a lumen that can be a central, axial lumen. In some embodiments, the intermediate shaft 140 can be sized and/or shaped to slidably fit within the lumen 802 (shown in FIG. 8) of the outer shaft 138 such that the intermediate shaft 140 and the outer shaft 138 are coaxial. Similarly, in some embodiments, the inner shaft can be sized and/or shaped to slidably fit within the lumen 804 (shown in FIG. 8) of the intermediate shaft 140 such that the inner shaft and the intermediate shaft 140 are coaxial. In this configuration, each of the outer shaft 138, the intermediate shaft 140, and the inner shaft can be displaced relative to the others of the outer shaft 138, the intermediate shaft 140, and the inner shaft.

In some embodiments, each of the outer shaft 138, the intermediate shaft 140, and the inner shaft can have the same length, and in some embodiments some or all of the outer shaft 138, the intermediate shaft 140, and the inner shaft can have different lengths. In some embodiments, for example, the intermediate shaft 140 can be relatively longer than the outer shaft 138, and in some embodiments, the inner shaft can be relatively longer than the intermediate shaft 140.

The thrombus extraction catheter 104 can further include a thrombus extraction device (TED). The TED can connect to the intermediate shaft 140 and the inner shaft, and can be contained in an undeployed configuration within the lumen 802 of the outer shaft 138. In some embodiments, the relative positioning of the outer shaft 138, the intermediate shaft 140, and/or the inner shaft can result in the TED being in an undeployed configuration, a deployed configuration, a partial expansion configuration, and/or a full expansion configuration. In some embodiments, the TED in the deployed configuration can be in either the full expansion configuration or in the partial expansion configuration.

The handle 134 can include a distal end 142, also referred to herein as a lock end 142, and a proximal end 144, also referred to herein as a plunger end 144. In some embodiments, the intermediate shaft 140 connects to, and distally extends towards the distal end 132 of the thrombus extraction catheter 104 from the distal end 142 of the handle 134.

As seen in FIG. 1, the distal end 142 of the handle 134 can include a lock feature 146 such as, for example, a spinlock. The lock feature 146 can selectively engage and/or lockingly engage with a mating feature 148 located on a proximal end 150 of the outer sheath 138. In some embodiments, for example, the outer sheath 138 can proximally slide over the intermediate sheath 140 until the lock feature 146 engages with the mating feature 148 to thereby secure the position of the outer sheath 138 with respect to the intermediate sheath 140. In embodiments in which the intermediate shaft 146 is relatively longer than the outer shaft 138, a portion of the intermediate shaft 146 distally extends from a distal end 152 of the outer shaft 138 when the outer shaft 138 is lockingly engaged with the lock feature 146.

The handle 134 can include a plunger 154 that can be movable between a first, non-extended position and a second, extended position. In some embodiments, the plunger 154 can be moved from the first position to the second position by proximally displacing the plunger 154 relative to the handle 134. The plunger 154 can be lockable in one or both of the first position and/or the second position.

The plunger 154 can connect to the inner shaft such that the inner shaft is displaceable relative to the handle 134, the outer shaft 138, and/or the intermediate shaft 140 via the movement of the plunger 154 from the first position to the second position. In some embodiments in which the inner shaft is relatively longer than the intermediate shaft 140 and/or the outer shaft 138, the inner shaft can have a length such that the inner shaft distally extends past a distal end of the intermediate shaft 140 regardless of whether the plunger 154 is in the first position or the second position.

The thrombus extraction catheter 104 can further include a first flush port 155 connecting to the outer shaft 138 and a second flush port 156 connecting to the handle 134. In some embodiments, the first flush port 155 can be fluidly connected to the lumen 802 of the outer shaft 138 so as to allow the flushing of the lumen 802 of the outer shaft 138 via the first flush port 155. In some embodiments, the second flush port 156 can be fluidly connected to an internal portion of the handle 134 and thereby the lumen of the intermediate shaft 140 so as to allow the flushing of the lumen of the intermediate shaft 140.

The thrombectomy system 100 can further include a loading funnel 158. The loading funnel 158 can include a funnel portion 160 and a shaft portion 162. The funnel portion 160 can define a funnel shaped interior volume connecting to a lumen of the shaft portion 162. The funnel shaped interior volume can be sized and shaped to receive the self-expanding funnel and to move the self-expanding funnel to a constrained position as the self-expanding funnel is advanced through the funnel portion 160. The funnel shaped interior volume and the lumen can be sized to allow the distal end 124 of the obturator 120 to pass completely through the loading funnel 158.

In some embodiments, the loading funnel 158 can be configured to facilitate loading of the self-expanding funnel into the obturator 102. In some embodiments, the self-expanding funnel can be loaded by inserting the obturator 120 through the elongate member 106 such that the obturator 120 extends from the distal end 110 of the elongate member 106 and beyond the self-expanding funnel. The loading funnel 158 can then be proximally slid over the obturator 120 and the self-expanding funnel until the self-expanding funnel is fully encapsulated by the loading funnel 158 and/or until the self-expanding funnel is in the constrained configuration. The obturator 120 can then be retracted to thereby load and/or capture the self-expanding funnel within a portion of the obturator 120, and the loading funnel 158 can then be removed from the obturator 120 and the elongate member 106.

Figure 2:
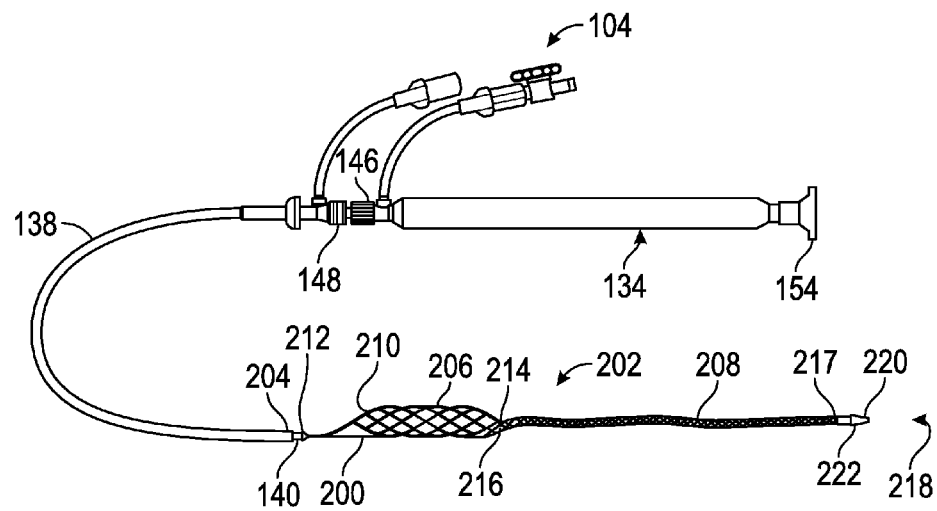
FIG. 2 is a side view of one embodiment of the thrombus extraction catheter having a thrombus extraction device is a deployed configuration.

The thrombectomy system 100 can further include a sealed hub dilator 170, also referred to herein as a seal dilator 170 and/or an aperture dilator 170. A section view of seal dilator 170 is shown in FIG. 1. The seal dilator 170 can be sized and shaped for insertion into the sealed aperture 112 prior to removal of thrombus through the sealed aperture 112. By this insertion into the sealed aperture 112, the seal dilator 170 can dilate the sealed aperture 112. In some embodiments, this dilation of the sealed aperture 112 can prevent the application of force from the sealed aperture 112 onto the thrombus during removal of the thrombus through the sealed aperture 112. In some embodiments, the seal dilator 170 can comprise an insertion portion 172 configured to facilitate the insertion of the seal dilator 170 into the sealed aperture 112. The seal dilator 170 can further comprise a body portion 174 that can, alone, or together with the insertion portion 172 define an extraction lumen 176 through which the thrombus can be removed from the lumen 1701 of the elongate member 106. In some embodiments, the internal diameter of the extraction lumen 176 can be larger than a diameter of the sealed aperture 112 in a sealed configuration With reference now to FIG. 2, a side view of one embodiment of the thrombus extraction catheter 104 is shown. The thrombus extraction catheter 104 includes the handle 134, the outer shaft 138, the intermediate shaft 140, the inner shaft 200, and the thrombus extraction device 202, also referred to herein as the TED 202. As shown in FIG. 2, the outer shaft 138 is proximately displaced relative to the handle 134 such that the mating feature 148 of the outer shaft 138 is contacting the locking feature 146 of the handle 134. Due to this positioning of the outer shaft 138 with respect to the handle 134, each of the intermediate shaft 140, the inner shaft 200, and the TED 202 distally extend beyond a distal end 204 of the outer shaft 138. The thrombus extraction device 202 shown in FIG. 2 is in a deployed and partial expansion configuration.

The thrombus extraction device 202 can include a self-expanding coring element 206, and an expandable cylindrical portion 208. The self-expanding coring element 206 can be relatively more proximally located on the thrombus extraction catheter 104 than the expandable cylindrical portion 208. The self-expanding coring element 206 can include a proximal end 210 connecting to a distal end 212 of the intermediate shaft 140 and a distal end 214 connecting to a proximal end 216 of the expandable cylindrical portion 208. The distal end 217 of the expandable cylindrical portion 208 can connect to a distal end 218 of the inner shaft 200.

In some embodiments, the distal end 218 of the inner shaft 200 can further include a tip 220 such as an atraumatic tip and/or a radiopaque marker 222. In some embodiments, the tip 220 can include the radiopaque marker 222. Further radiopaque markers can be located on, for example, the outer shaft 138 and specifically the distal end 204 of the outer shaft 138 and/or the distal end 212 of the intermediate shaft 140. In some embodiments, one or both of the distal end 204 of the outer shaft 138 and the distal end 212 of the intermediate shaft 140 can each comprise a radiopaque marker. In some embodiments, the atraumatic tip 220 can define a channel configured to allow the guidewire to pass through the atraumatic tip 220.

Figure 3:
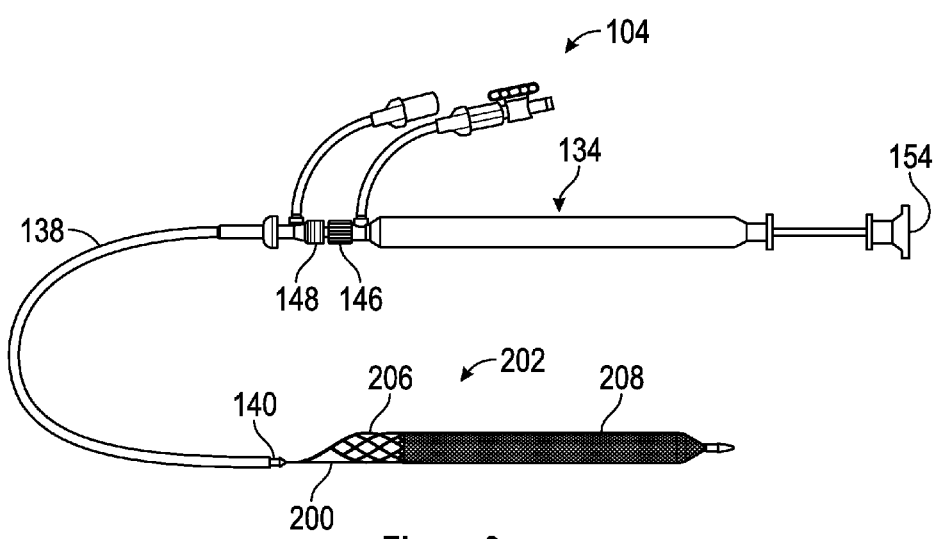
FIG. 3 is a side view of one embodiment of the thrombus extraction catheter having a thrombus extraction device is a deployed configuration at full expansion.

With reference now to FIG. 3, a side view of one embodiment of the thrombus extraction catheter 104 with the thrombus extraction device 202 in the deployed and full expansion configuration is shown. In contrast to the embodiment of FIG. 2, the plunger 154 is in the second position, proximally retracted from the handle 134, and the inner shaft 200 is thereby proximally retracted relative to the intermediate shaft 140 to thereby fully expand the expandable cylindrical portion 208 and two secure the expandable cylindrical portion 208 and the self-expanding coring element 206 in full expansion configurations and/or in full expansion.

The thrombus extraction catheter 104 can comprise one or several features configured to secure the thrombus extraction device 202, and specifically the self-expanding coring element 206 and/or the expandable cylindrical portion 208 in a fully expanded position and/or in full expansion. As used herein, full expansion occurs when the thrombus extraction device 202 is deployed and when the plunger 154 is in the second position. In some embodiments, one or several dimensions of the thrombus extraction device 202 can vary when the thrombus extraction device 202 is in full expansion. In some embodiments, this can facilitate apposition of the walls of the blood vessel by the thrombus extraction device 202 and/or a desired force or force level applied to the walls of the blood vessel by the thrombus extraction device 202.

In some embodiments, the plunger 154 can be locked in the second position by, for example, rotating the plunger 154 with respect to the handle 134 to thereby engage one or several locking features on the plunger 154 and in the handle 134. In some embodiments, by locking the plunger 154 in the second position, the thrombus extraction device 202, and specifically the self-expanding coring element 206 and/or the expandable cylindrical portion 208 can be secured in the full expansion by securing the position of the inner shaft 200 with respect to the intermediate shaft 140. In some embodiments, securing the position of the inner shaft 200 with respect to the intermediate shaft 140 can include locking the inner shaft 200 with respect to the intermediate shaft 140 and/or coupling the position of the inner shaft 200 with respect to the position of the intermediate shaft 140. In some embodiments, this locking and/or coupling can be static, referred to herein as statically locked and/or statically coupled, in that the position of the inner shaft 200 is fixed with respect to the position of the intermediate shaft 140, and in some embodiments, this locking and/or coupling can be dynamic, referred to herein as dynamically locked and/or dynamically coupled, in that the position of the inner shaft 200 with respect to the intermediate shaft 140 is limited. In some embodiments, and as will be discussed at greater length below, the inner shaft 200 can be dynamically locked to the plunger 154 via a compliance spring 1214 which allows some movement of the inner shaft 200 with respect to the intermediate shaft 140 when the plunger is locked in the second position. Thus, in such an embodiment, the inner shaft 200 is dynamically locked and/or dynamically coupled to the intermediate shaft 140 and/or with respect to the intermediate shaft 140.

Figure 4:
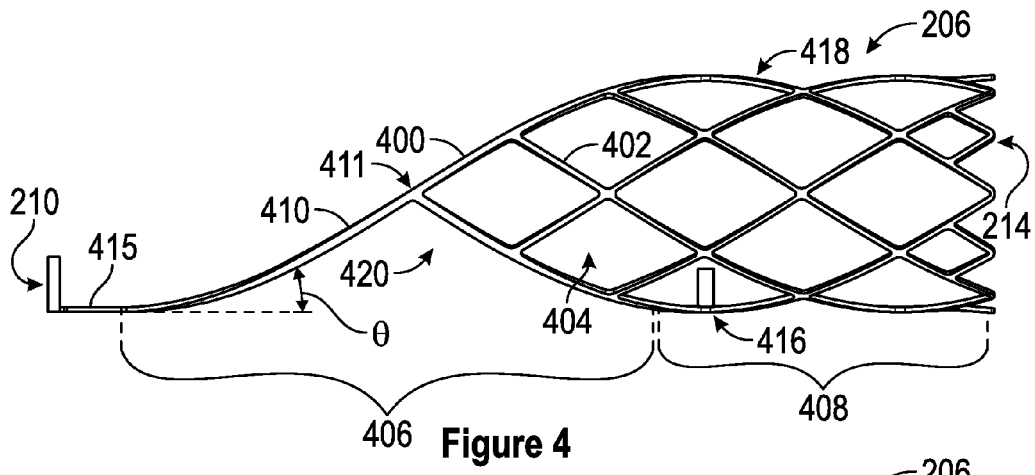
FIG. 4 is a side view of one embodiment of a self-expanding coring element.

With reference now to FIG. 4, a side view of one embodiment of the self-expanding coring element 206 is shown. The self-expanding coring element 206 can comprise a variety of shapes and sizes and can be made from a variety of materials. In some embodiments, the self-expanding coring element can be made from a shape memory material such as, for example, a shape memory alloy and/or a shape memory polymer. In some embodiments, the self-expanding coring element 206 can comprise a nitinol and/or a nitinol alloy.

The self-expanding coring element 206 can be made using a variety of techniques including, for example, welding, laser welding, cutting, laser cutting, expanding, or the like. In some embodiments, the self-expanding coring element 206 can be laser cut from a piece of nitinol such as, for example, a nitinol tube, after which the self-expanding coring element 206 can be blown up and/or expanded.

The self-expanding coring element 206 can comprise a unitary fenestrated structure 400 and/or a stent or a stent portion that can be configured to core and separate a portion of a thrombus such as a vascular thrombus from the blood vessel containing the thrombus. This unitary fenestrated structure 400 can comprise a plurality of struts 402 that together define a plurality of interstices 404. The struts can comprise a variety of shapes and sizes, and in some embodiments, the struts can have a thickness and/or diameter between approximately 0.05 and 0.15 inches, between approximately 0.075 and 0.125 inches, between approximately 0.09 and 0.1 inches, and/or of approximately 0.096 inches.

Figure 5:
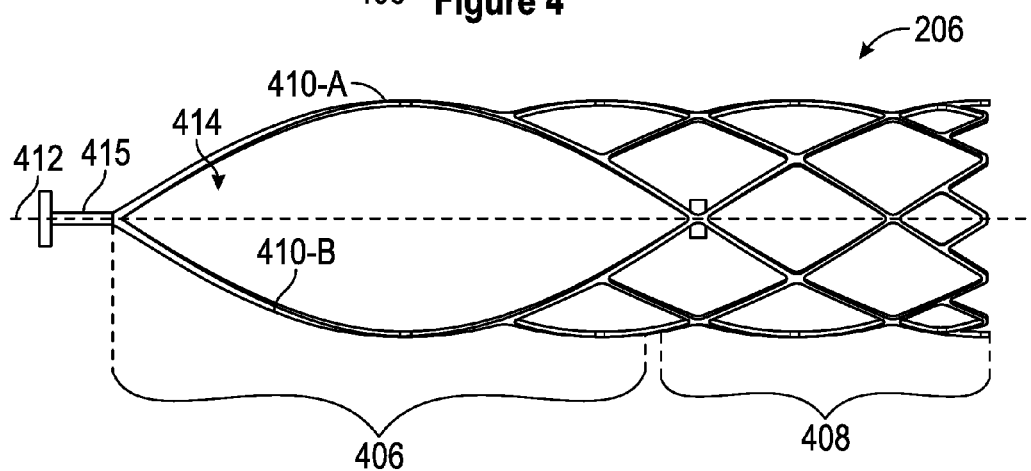
FIG. 5 is a top view of one embodiment of a self-expanding coring element.
Figure 6:
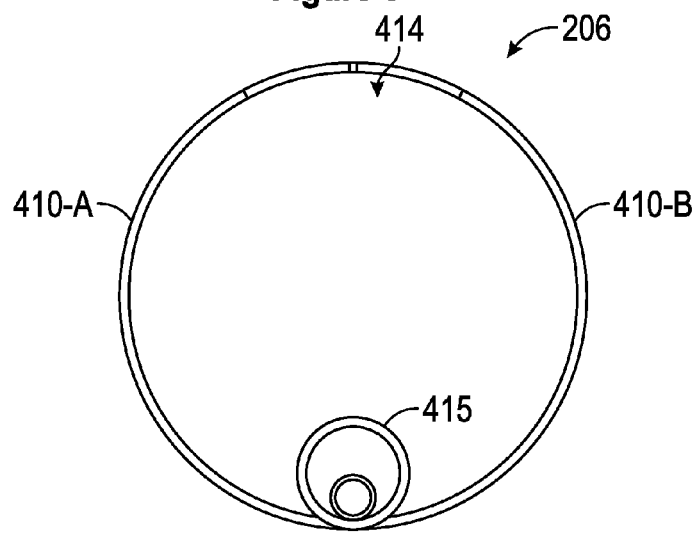
FIG. 6 is a front view of one embodiment of a self-expanding coring element.

In some embodiments, the self-expanding coring element 206 can comprise a first region 406 and a second region 408. The second region 408 can be generally tubular and can include a plurality of interconnected struts 402. The first region 406, as seen in FIG. 5, can comprise a reduced number of struts 402 as compared to the second region to facilitate the collapse of the self-expanding coring element 206 to a non-expanded configuration and to maintain a coring orientation when the blood vessel is tortuous. In some embodiments, the first region can further comprise two curved struts 410-A, 410-B twisting in opposite directions around a central axis 412, also referred to herein as a longitudinal axis 412, of the self-expanding coring element 206 to define a mouth 414 of the self-expanding coring element 206.

In some embodiments, the connection of the self-expanding coring element 206 to the intermediate shaft 140 via the two curved struts 410-A, 410-B can improve the operation of the thrombus extraction device 202 by flexibly connecting the self-expanding coring element 206 to the intermediate shaft 140. Particularly, the removal of struts from region 420 of the self-expanding coring element 206 allows the self-expanding coring element 206 to flex about a connection member 415 located at the proximal end 210 of the self-expanding coring element 206 and connecting the self-expanding coring element 206 to the intermediate shaft 140 of the thrombus extraction catheter 104. This ability to flex can facilitate the maintenance of the coring orientation with the blood vessel is tortuous. In some embodiments, such flexing of the self-expanding coring element 206 can result in the region 420 functioning as the mouth 414.

As seen in FIG. 4, the curved struts 410 extend at an angle θ, also referred to herein as a coring angle, relative to the central axis 412 from a bottom 416 of the self-expanding coring element 206 towards the top 418 of the self-expanding coring element 206. In some embodiments, this angle can be between 20 degrees and 50 degrees and/or between 30 degrees and 45 degrees when fully expanded.

In some embodiments, the coring angle can either positively or adversely affect the operation of the TED 202. For example, too steep a coring angle can prevent the self-expanding coring element 206 from being collapsible and thus prevent the retraction of the self-expanding coring element 206 into the introducer sheath 102. Additionally, too shallow a coring angle can result in the self-expanding coring element 206 too easily collapsing which can decrease the coring ability of the self-expanding coring element 206. In some embodiments, this decrease in the coring ability of the self-expanding coring element 206 can result in the self-expanding coring element 206 no longer effectively coring thrombus.

In some embodiments, the most proximal edge of the two curved struts 410-A, 410-B, referred to herein as a leading edge 411, can be sharpened and/or the leading edge 411 of the two curved struts 410-A, 410-B can comprise a cutting element, knife, or the like The self-expanding coring element 206 can comprise a variety of sizes. In some embodiments, the self-expanding coring element 206 can comprise a length, defined as the shortest distance between the proximal end 210 of the self-expanding coring element 206 and the distal end 214 of the self-expanding coring element 206, of between approximately one and 3 inches, between approximately 1.5 and 2.5 inches, between approximately 1.75 and 2.25 inches, between approximately 1.9 2.0 inches, and/or of approximately 1.96 inches. In some embodiments, the self-expanding coring element 206 can comprise a fully expanded diameter between approximately 2 and 50 mm, between approximately 4 and 25 mm, between approximately 6 and 20 mm, and/or between approximately 8 and 16 mm. In some embodiments, the self-expanding coring element can be applied to debulking of an artery or vein such as, for example, the inferior vena cava. In some embodiments, such debulking can be performed in response to the occluding and/or partial occluding of one or several filters in the inferior vena cava.

In some embodiments, the length and the diameter of the self-expanding coring element 206 can be selected based on the size of the blood vessel, and particularly the diameter of the blood vessel from which thrombus is to be extracted. In some embodiments, the length of the self-expanding coring element 206 can be selected based on the fully expanded diameter of the self-expanding coring element 206 to prevent undesired tipping and/or rotation of the self-expanding coring element within the blood vessel and with respect to the blood vessel. As used anywhere herein, "approximately"

refers to a range of +/− 10% of the value and/or range of values for which "approximately" is used.

Figure 7:
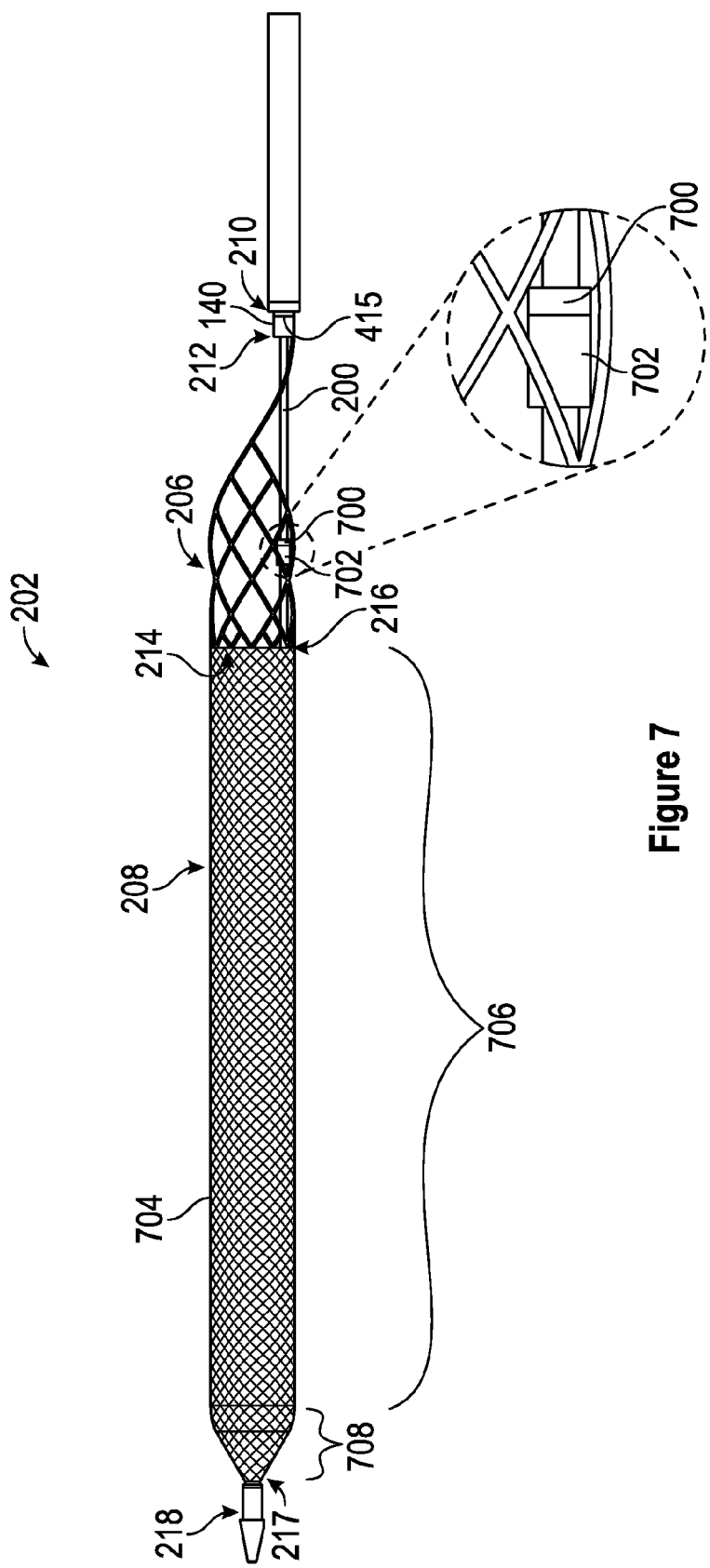
FIG. 7 is a side view of one embodiment of the thrombus extraction device in a full expansion configuration.

With reference now to FIG. 7, a side view of one embodiment of the thrombus extraction device 202 is shown. As seen in FIG. 7, the self-expanding coring element 206 is connected via the connection member 415 at the proximal end 210 of the self-expanding coring element 206 to the distal end 212 of the intermediate shaft 140. The proximal end 216 of the expandable cylindrical portion 208 connects to the distal end 214 of the self-expanding coring element 206. In some embodiments, the expandable cylindrical portion 208 and specifically the proximal end 216 of the expandable cylindrical portion 208 is formed on the distal end 214 of the self-expanding coring element 206 to thereby form a unitary thrombus extraction device 202. The distal end 217 of the expanding cylindrical portion 208 connects to the distal end 218 of the inner shaft 200.

In some embodiments, and as seen in FIG. 7, the self-expanding coring element 206 can engage with all or portions of the inner shaft 200 to affect the expansion of the self-expanding coring element 206. Specifically, in some embodiments, the self-expanding coring element 206 can include a ring 700, also referred to herein as a ring feature 700. The ring 700 can be the same material as the self-expanding coring element 206 or can be a different material than the self-expanding coring element 206. The ring 700 can be integrally formed with the self-expanding coring element 206 and/or can be attached to the self-expanding coring element via, for example, one or several welds, adhesive, one or several mechanical fasteners, or the like. The ring 700 can have a diameter larger than the diameter of the inner shaft 200 such that the ring 700 is slidable along the inner shaft 200.

As further seen in FIG. 7, the inner shaft 200 can include a stop 702. In some embodiments, the stop 702 can comprise a polymeric member and/or metallic member that is affixed to a portion of the inner shaft 200. In some embodiments, the stop 702 can be sized and shaped to engage with the ring 700 to thereby apply proximally directed force to the self-expanding coring element 206 when the inner shaft 200 is proximally displaced via movement of the plunger 154 to the second position. In some embodiments, a portion of the self-expanding coring element 206 located between the ring 700 and the connection member 415 can be forcibly expanded by the application of this proximally directed force to ring 700, thereby moving the self-expanding coring member 206 to full expansion.

In some embodiments, the inner shaft 200 of the thrombus extraction catheter 104 can be selectively connected to the distal end 217 of the expandable cylindrical portion 208. This can allow the displacement of the inner shaft 200 to bring the self-expanding coring element 206 to full expansion via the engagement of the ring feature 700 with the stop 702. In some embodiments, and after the self-expanding coring element 206 is at full expansion, the inner shaft 200 can be recoupled to the distal end 217 of the expandable cylindrical portion 208 such that the expandable cylindrical portion 208 is fully expanded and/or can be recoupled to the distal end 217 of the expandable cylindrical portion 208 such that the expandable cylindrical portion 208 to compress the expandable cylindrical portion 208 when the plunger 154 is moved from the second position to the first position.

In some embodiments, the expandable cylindrical portion 208 can comprise a braided filament mesh structure 704 that can be configured to capture thrombus. In some embodiments, the braided filament mesh structure can be coextensive with the expandable cylindrical portion 208 and thus can share a proximal end 216 and/or a distal end 217. In the embodiment shown in FIG. 7, the braided filament mesh structure 704 is a braid of elastic filaments having a generally tubular, elongated portion 706 and a distal tapered portion 708. In other embodiments, the braided filament mesh structure 704 can be any porous structure and/or can have other suitable shapes, sizes, and configurations (e.g., the distal portion 708 can be generally cylindrical, etc.).

Due to the connection of the braided filament mesh structure 704 to the distal end 218 of the inner shaft 200, axial movement of the inner shaft 200 radially expands/shortens and collapses/lengthens the braided filament mesh structure 704 of the TED 200. For example, so long as the intermediate shaft 140 is fixed and/or limited to axial movement at a rate less than that of the inner shaft 200: (1) distal movement of the inner shaft 200 stretches the braided filament mesh structure 704 along its longitudinal axis such that the radius of the braided filament mesh structure 704 decreases and the length of the braided filament mesh structure 704 increases; and (2) proximal movement of the inner shaft 200 compresses the braided filament mesh structure 704 along its longitudinal axis such that the radius of the braided filament mesh structure 704 increases and the length of the braided filament mesh structure 704 decreases. In certain embodiments, the braided filament mesh structure 704 can have a length in the collapsed configuration between approximately 5 and 30 inches, between approximately 10 and 20 inches, and/or of approximately 16 inches, and in some embodiments, the braided filament mesh structure 704 can have a length in the expanded configuration of between approximately 1 and 25 inches, between approximately 10 and 20 inches, and/or of approximately 11 inches.

In some embodiments, the braided filament mesh structure 704 can be formed by a braiding machine and/or weaving machine, and in some embodiments, the braided filament mesh structure 704 can be manually braided and/or woven. In some embodiments, the braided filament mesh structure 704 may be formed as a tubular braid, which tubular braid may then be further shaped using a heat setting process. In some embodiments, the braid may be a tubular braid of fine metal wires such as nitinol (nickel-titanium alloy), platinum, cobalt-chrome alloy, stainless steel, tungsten or titanium. In some embodiments, the braided filament mesh structure 704 can be formed at least in part from a cylindrical braid of elastic filaments. Thus, the braid may be radially constrained without plastic deformation and will self-expand on release of the radial constraint. Such a braid of elastic filaments is herein referred to as a "self-expanding braid."

In some embodiments, the thickness of the braid filaments can be less that about 0.15 mm. In some embodiments, the braid may be fabricated from filaments and/or wires with diameters ranging from about 0.05 mm to about 0.25 mm. In some embodiments, braid filaments of different diameters may be combined to impart different characteristics including: stiffness, elasticity, structure, radial force, pore size, embolic capturing or filtering ability, etc. In some embodiments, the braided filament count is between 20 and 80, is greater than 30, and/or is approximately 24. Pore sizes of the braided mesh in the elongated portion 706 may be in the range of about 0.4 mm to 4.0 mm. In some embodiments, the pore size may be in the range of 0.5 mm to 2.5 mm.

Figure 10:
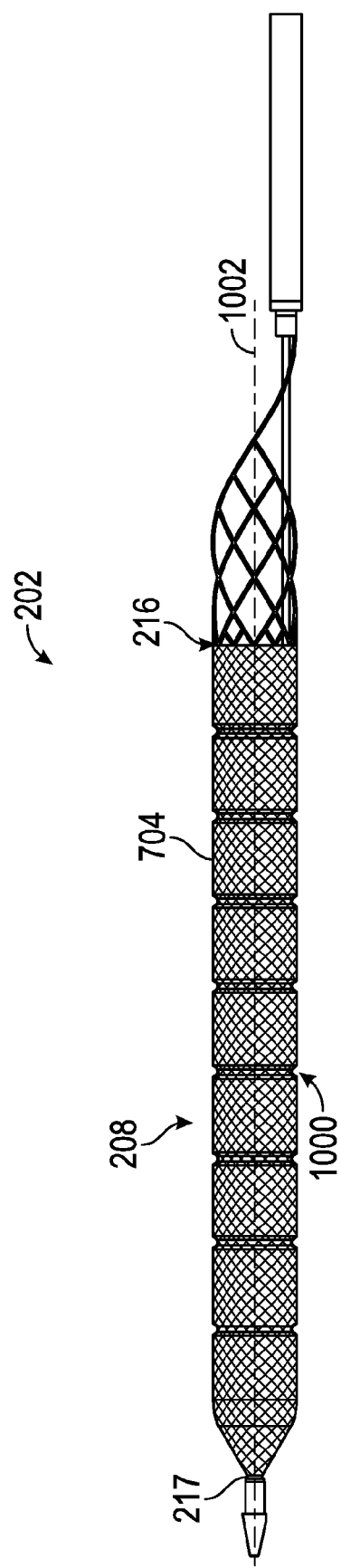
FIG. 10 is a side view of one embodiment of the thrombus extraction device including a plurality of circumferential grooves.

In some cases thrombus may form a shape that is difficult to retract into the introducer sheath 102 when thrombus is within the braided filament mesh structure 704. Such a case is depicted in FIG. 8 in which the thrombus extraction device 202, and specifically the braided filament mesh structure 704, is partially retracted into the introducer sheath 102. As depicted in FIG. 8, thrombus 800 has formed a ball that has a diameter larger than the diameter of the introducer sheath 102. Such behavior by the thrombus 800 can prevent the removal of the TED 200 and the thrombus 800 from the patient's body. FIGS. 9 and 10 address features to prevent such behavior by the thrombus.

FIG. 8 further shows a cross-section view of the elongate member 106 such that the lumen 1702 of the elongate member is visible, a cross-section of the outer shaft 138 such that the lumen 802 of the outer shaft 138 is visible, and a cross-section of the intermediate shaft 140 such that the lumen 804 of the intermediate shaft 140 is visible.

With reference now to FIG. 9, a side view of one embodiment of the braided filament mesh structure 704 comprising multiple pore sizes is shown. As seen, the braided filament mesh structure 704 comprises a first portion 900 comprising a first plurality of pores 904 and a second portion 902 comprising a second plurality of pores 906. In some embodiments, the first portion 900 can correspond to the elongated portion 706, and the second portion 902 can correspond to the distal tapered portion 708.

As shown in FIG. 9, the first portion 900 of the braided filament mesh structure 704 is relatively more proximal than the second portion 902. As further shown, the pores in the first plurality of pores 904 of the first portion 900 are smaller than the pores in the second plurality of pores 906 of the second portion 902. In some embodiments, the larger pores of the distal, second portion 902 can have an average size greater than or equal to 1.5 mm, and in some embodiments, between approximately 1.0 mm and 4.0 mm.

In such an embodiment, the larger size of the pores of the second plurality of pores 906 can allow and/or facilitate the extrusion of portions of the thrombus when the braided filament mesh structure 704 is moved to the unexpanded configuration and/or when the braided filament mesh structure 704 is retracted into the introducer sheath 102. In some embodiments, this extrusion of portions of the thrombus can prevent the case in which the thrombus cannot be retracted into the introducer sheath 102. Further, in some embodiments, relatively newer portions of thrombus can be extruded before relatively older portions of thrombus as relatively newer portions of thrombus can be softer and/or more malleable. These relatively newer portions of the thrombus can then be captured and/or broken down by features of the introducer sheath 102.

With reference now to FIG. 10, a side view of one embodiment of the TED 200 comprising a plurality of circumferential depressions 1000, also referred to herein as circumferential grooves, radial ribs, and/or radial grooves, is shown. In some embodiments, some or all of this plurality of circumferential depressions 1000 can inwardly extend towards a central axis 1002 and/or midline 1002 of the thrombus extraction device 202. In some embodiments, the plurality of circumferential depressions 1000 can be longitudinally spaced and/or equally spaced along the length of the expandable cylindrical portion 208 and/or the braided filament mesh structure 704 between the proximal end 216 and the distal end 217 of the cylindrical portion 208 and/or the braided filament mesh structure 704. In some embodiments, these circumferential depressions 1000 can, when the thrombus extraction device 202 is moved from an expanded configuration to an unexpanded configuration, engage with portions of the thrombus contained within the cylindrical portion 208 and/or the braided filament mesh structure 704 to inhibit movement of the thrombus with respect to one or both of the proximal end 216 and the distal end 217 of the cylindrical portion 208 and/or the braided filament mesh structure 704. This inhibition of thrombus movement can decrease the likelihood of the creation of thrombus that cannot be retracted into the introducer sheath 102.

Although depicted in separate figures, some embodiments of the thrombus extraction device 202 can include both the plurality of circumferential depressions discussed with respect to FIG. 10 and multiple pore sizes as discussed with respect to FIG. 9.

Figure 11:
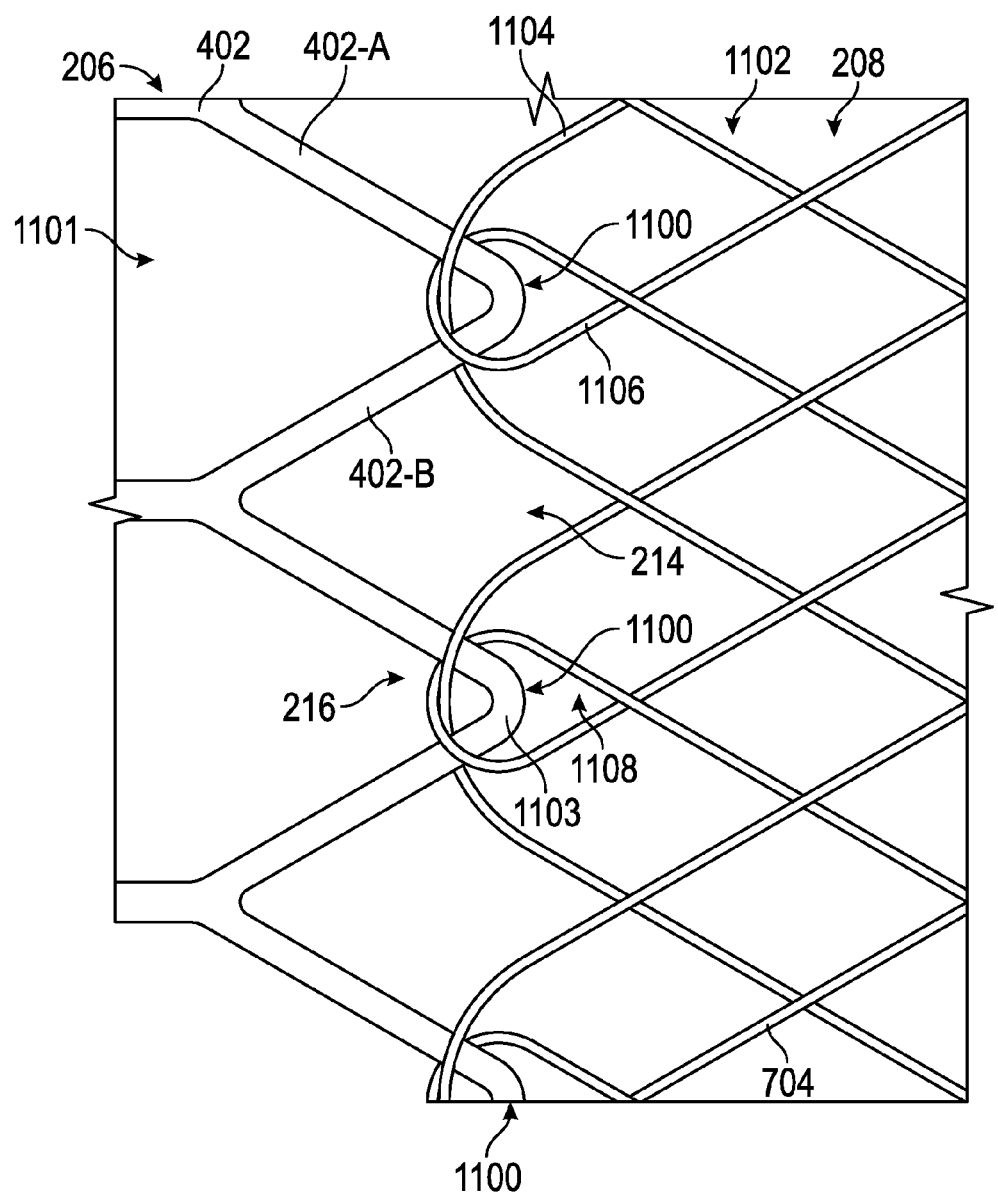
FIG. 11 is a schematic illustration of one embodiment of a weaving pattern for forming the cylindrical portion and/or the braided filament mesh structure onto the self-expanding coring element.

With reference now to FIG. 11, a schematic illustration of one embodiment of a weaving pattern for forming the cylindrical portion 208 and/or the braided filament mesh structure 704 onto the self-expanding coring element 206 at one or several formation points 1103 is shown. As seen, the self-expanding coring element 206 comprises a plurality of struts 402 that connect at formation points 1103 comprising peaks 1100, also referred to herein as peak struts 1100. As seen, each of the peaks 1100 is formed by the intersection of a first strut 402-A and a second strut 402-B, which intersecting struts 402-A, 402-B form a peak aperture 1101.

In some embodiments, the self-expanding coring element 206 can comprise a plurality of peaks 1100 extending around the distal end of the self-expanding coring element 206. The plurality of peaks 1100 can comprise 4 peaks 1100, 6 peaks 1100, 8 peaks 1100, 10 peaks 1100, 12 peaks 1100, 16 peaks 1100, 20 peaks 1100, 24 peaks 1100, between 4 and 50 peaks, between 8 and 20 peaks, and/or any other or intermediate number of peaks.

The cylindrical portion 208 and/or the braided filament mesh structure 704 can comprise a plurality of filaments 1102 woven and/or braided together to form the cylindrical portion 208 and/or the braided filament mesh structure 704. In some embodiments, the plurality of filaments can include, for each of the peaks 1100 of the self-expanding coring element 206, a first filament 1104 and the second filament 1106. The first and second filaments 1104, 1106 can be woven onto their respective peak. In some embodiments, the first and second filaments 1104, 1106 can be woven onto their respective peak such that one or both of the first and second filaments 1104, 1106 form a loop about their respective peak. Thus, in some embodiments, the only the first filament 1104 forms a look about its peak, only the second filament 1106 forms a loop about its peak, or both the first and second filaments 1104, 1106 form loops about their peak. With reference to the embodiment of FIG. 11, the first filament 1104 can be inserted straight through the peak aperture 1101 of its peak such that the first filament 1104 does not loop on itself directly adjacent to its peak, and more specifically, directly distal of its peak.

The first filament 1104 can be inserted through the peak aperture 1101 of its peak 1100 such that the first filament 1104 passes, when looking from the outside of the self-expanding coring element 206 towards the inside of the self-expanding coring element 206, on top of the first strut 402-A and under the second strut 402-B.

The second filament 1106 can be inserted through the peak aperture 1101 of its peak such that the portion of the second filament 1106 passing through the peak aperture 1101 is separated from the peak by the first filament 1104. Further, the second filament 1106 can be inserted through the peak aperture 1101 such that the second filament 1106 passes underneath the first strut 402-A and over the second strut 402-B. after insertion through the peak aperture 1101, the second filament 1106 can be looped on itself to form a loop 1108 directly distal to its peak 100.

In some embodiments, because each filament 1104, 1106 is inserted through a peak aperture 1101, each filament 1104, 1106 can be treated, for braiding or weaving purposes as comprising a first wire extending from its peak 1100 to a first end of the filament 1104, 1106 and a second wire extending from its peak to a second end of that filament 1104, 1106. Thus, in some embodiments in which the self-expanding coring portion 206 comprises 12 peaks, the cylindrical portion 208 and/or the braided filament mesh structure 704 can be formed from 24 filaments 1104, 1106 which can be woven and/or braided as 48 wires to form a 48 wire mesh and/or weave.

In some embodiments, the cylindrical portion 208 and/or the braided filament mesh structure 704 can be braided/woven by, identifying the plurality of formation points 1103 formed by some of the struts 402 of the self-expanding coring element 206. Unique pairs of wires can be threaded through each of the formation points 1103, and specifically through the peak aperture 1101 adjacent to each of the formation points 1103. In some embodiments, each unique pair of wires can comprise a first wire 1104 and a second wire 1106 overlaying the first wire 1104. The first and second wires can then be woven into a net-like filament mesh structure of the cylindrical portion 208 and/or the braided filament mesh structure 704 from the unique pairs of wires such that the first wires 1104 do not form loops about the formation points 1103 through which the first wires 1104 are threaded and such that the second wires 1106 form loops 1108 about the formation points 1103 through which the second wires 1106 are threaded.

Figure 12:
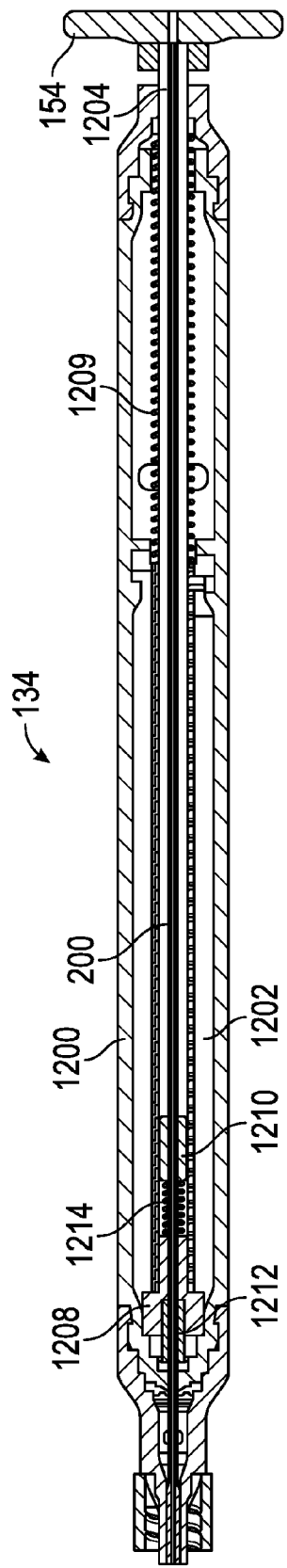
FIG. 12 is a section view of an embodiment of the handle with a plunger in a first position.
Figure 13:
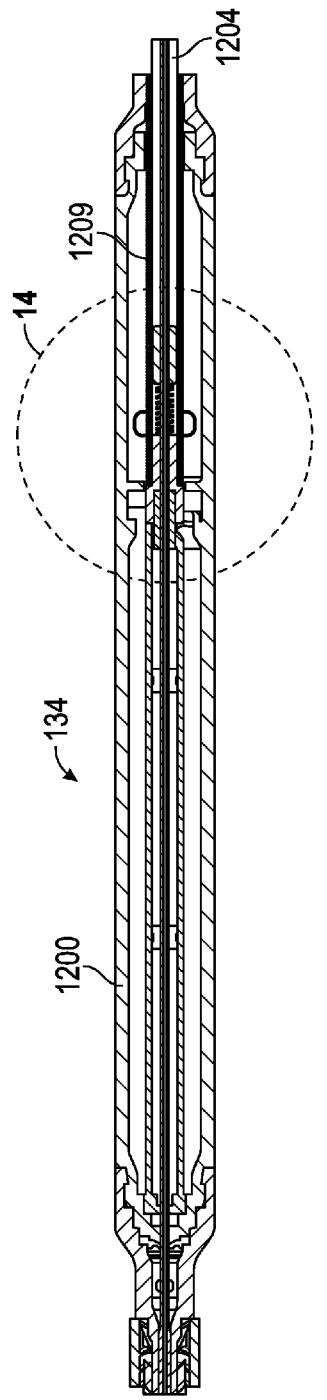
FIG. 13 is a section view of an embodiment of the handle with a plunger in a second position.

With reference now to FIG. 12, a section view of an embodiment of the handle 134 in which the plunger 154 is in the first position is shown, and with reference to FIG. 13 a section view of an embodiment of the handle 134 in which the plunger 154 is in the second position is shown. The handle 134 can include a housing 1200 that defines an internal volume 1202. A plunger shaft 1204 can extend through all or portions of the internal volume 1202 and can connect to the inner shaft 200, which inner shaft 200 can define the previously referenced lumen 1400, also referred to herein as inner shaft lumen 1400. The plunger shaft 1204 can terminate at a plunger guide 1208 that is affixed to the plunger shaft 1204. In some embodiments, and as seen in FIGS. 12 and 13, the plunger 154 can be biased towards a first position by a plunger spring 1209 which can engage a portion of the handle 134 and the plunger guide 1208. Thus, the plunger spring 1209 is less compressed when the plunger 154 is in the first position as is shown in FIG. 12, and the plunger spring 1209 is more compressed when the plunger 154 is in the second position as is shown in FIG. 13. In some embodiments, this bias towards the first position can create a bias in the thrombus extraction device 202 towards the partial expansion configuration.

Figure 14:
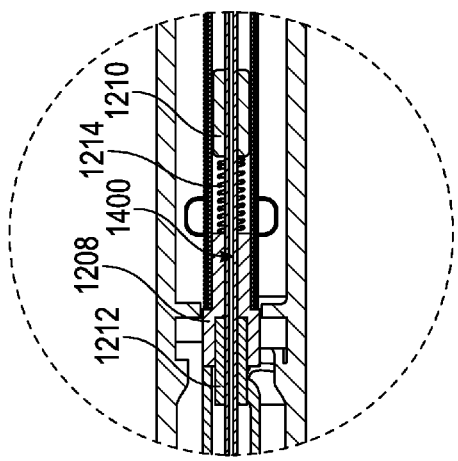
FIG. 14 is a close-up, section view of a portion of the handle with a plunger in a second position.

As seen in FIG. 14, a close-up view of the encircled portion "A" indicated in FIG. 13, the plunger guide 1208 can be positioned between a proximal stop 1210 and a distal stop 1212, which proximal stop 1210 and which distal stop 1212 can be each affixed to the inner shaft 200 including the inner shaft lumen 1400. The plunger guide 1208 can be dynamically connected to the proximal stop 1210 via a stent compliance spring 1214, also referred to herein as a compliance spring 1214. In some embodiments, the use of the compliance spring 1214 to connect the plunger guide 1208 and the proximal stop 1210 can allow a change in the diameter of the self-expanding coring element 206 according to compressive forces applied to the self-expanding coring element 206.

In some embodiments, for example, via the interaction of the ring feature 700 and the stop 702, radial compressive forces applied to the self-expanding coring element 206 can be transferred from the self-expanding coring element 206 via the ring feature 700 and the stop 702 to the compliance spring 1214. In embodiments in which the compressive force is greater than the spring force, the compliance spring 1214 can be compressed and the inner shaft 200 can distally advance relative to the intermediate shaft 140 to thereby reduce the diameter of the self-expanding coring element 206 until the compressive force is equal to the spring force. This compliance achieved via the compliance spring 1214 enables use of the thrombus extraction catheter 104 in blood vessels that can be arteries or venous vessels of non-constant diameter while maintaining desired contact of the self-expanding coring element 206 on the walls of the blood vessels, veins, or venous vessels. In some embodiments, this compliance can result in a constant outward force applied to the vessel walls by the self-expanding coring element 206 when the vessel has a diameter between approximately 1 and 30 mm, 2 and 25 mm, 5 and 20 mm and/or any other or intermediate diameter. In some embodiments, this constant outward force can be constant in that this outward force is within a predetermined range. In some embodiments, for example, the outward force can be approximately 5 N when the diameter of the self-expanding coring element 206 is approximately 20 mm and the outward force can be approximately 20 N when the diameter of the self-expanding coring element 206 is approximately 5 mm. Thus, in some embodiments, a locking mechanism which can include the plunger 154 and the compliance spring 1214 can be configured to maintain a desired radial force on a vessel wall when the stent is compressed by that vessel wall. In some embodiments, this desired force can be a sufficient radial force on the vessel wall to core and/or separate all or portions of thrombus from the vessel wall when the self-expanding coring element 206 is at full expansion.

Figure 15:
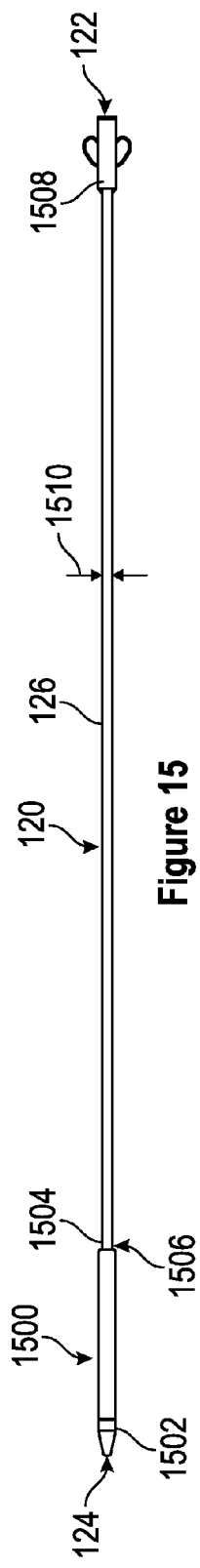
FIG. 15 is a side view of one embodiment of an obturator having a constant dimension of an elongate shaft.
Figure 16:
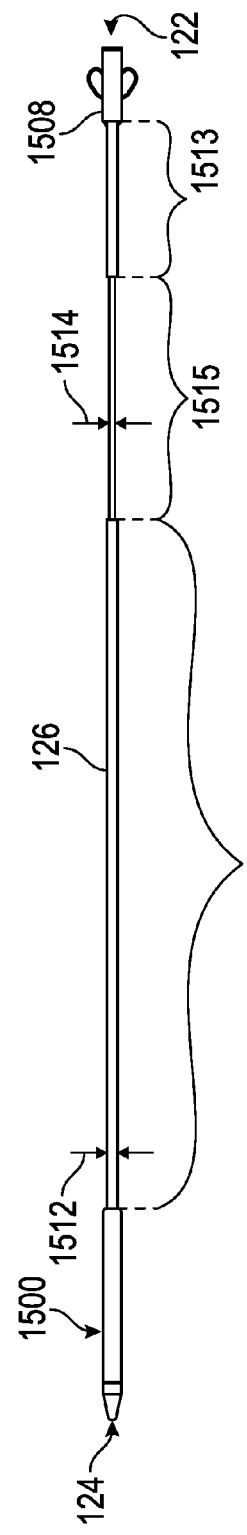
FIG. 16 is a side view of one embodiment of an obturator having a variable dimension of an elongate shaft.

With reference now to FIGS. 15 and 16, side views of embodiments of the obturator 120 are shown. As seen, the obturator 120 includes the proximal end 122, the distal end 124, and the elongate shaft 126. As further seen, the obturator 120 can include a capture sheath 1500 proximally extending form the distal end 124 of the obturator 120.

The Obturator 120 can further comprise a tip such as an atraumatic tip 1502 located at the distal end 124 of the obturator 120. In some embodiments, the atraumatic tip 1502 can be radiopaque. The obturator 120 can further include a connection fitting 1504 that can be located at a proximal end 1506 of the capture sheath 1500. In some embodiments, the connection fitting 1504 can be configured to sealingly connect with the distal end 110 of the elongate sheath 106 of the introducer sheath 102.

The obturator 120 can further include a stop portion 1508 located at the proximal end 122 of the obturator 120. In some embodiments, the stop portion 1508 can have a diameter larger than the lumen 1701 of the elongate member 106 of the introducer sheath 102 and/or larger than the diameter of the sealed aperture 112 located at the proximal end 108 of the introducer sheath 102 so as to prevent the stop portion 1508 from entering into the lumen 1701 of the elongate member 106 and/or the sealed aperture 112.

In some embodiments, the elongate shaft 126 can comprise a constant size and/or diameter, and in some embodiments, the elongate shaft 126 can comprise multiple sizes and/or diameters. For example, the diameter 1510 of the elongate shaft 126 shown in FIG. 15 is constant along the length of the elongate shaft 126. In contrast, the elongate shaft 126 shown in FIG. 16 has at least a first diameter 1512 along one or several first portions 1513 of the elongate shaft 126 and a second diameter 1514 along one or several second portions 1515 of the elongate shaft 126.

In some embodiments, the one or several second portions 1515 of the elongate shaft can be located along the length of the elongate shaft 126 such, that when the obturator 120 is received within the elongate member 106 of the introducer sheath 102 and positioned so that the connection fitting 1504 seals with the distal end 110 of the elongate sheath 106, the one or several second portions 1515 extend through the sealed aperture 112. In such an embodiment, the second diameter 1514 can be selected such that the one or several second portions do not contact and/or dilate the sealed aperture 112 and/or a seal within the sealed aperture 112. Because such an embodiment of the obturator 120 does not dilate the seal of the sealed aperture 112 when the one or several second portions extend through the sealed aperture 112, the introducer sheath 102 can be stored, package, and/or sold with such an obturator 120 pre-positioned extending through the lumen 1701 of the elongate member 106.

Figure 17:
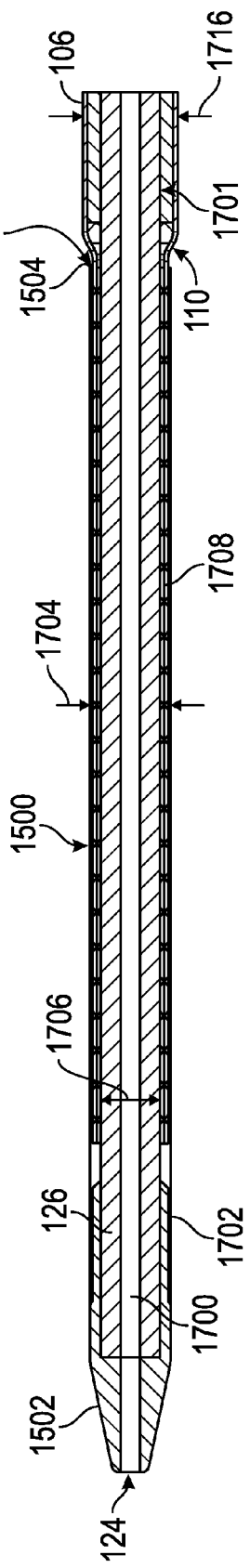
FIG. 17 is a detailed section view of one embodiment of the capture sheath of the obturator.

With reference now to FIG. 17, a detailed section view of one embodiment of the capture sheath 1500 is shown. As seen, the capture sheath 1500 includes the atraumatic tip 1502 and is connected to the elongate shaft 126 of the obturator 120, which elongate shaft 126 extends through a lumen 1701 of the elongate member 106. As further seen, a lumen 1700 extends through the atraumatic tip 1502 and the elongate shaft 126, which lumen 1700 can be configured to receive a guidewire.

That capture sheath 1500 includes a capture shell 1702 that distally extends from the atraumatic tip 1502 to the proximal end 1506 of the capture sheath 1500. The capture shell 1702 terminates in the connection fitting 1504. The capture shell 1702 has an internal diameter 1704 that is greater than a diameter 1706 of the portion of the elongate shaft 126 extending through the capture shell 1702. Due to the larger internal diameter 1704 of the capture shell 1500, a receiving space is created between the capture shell 1702 and the portion of the elongate shaft 126 extending through the capture shell 1702. In some embodiments, this receiving space can be sized and shaped to receive and/or retain a self-expanding funnel 1708 in a constrained configuration. In some embodiments, the self-expanding funnel 1708 can have a diameter matching the internal diameter 1704 of the capture shell 1702 when the self-expanding funnel 1708 is in the constrained configuration. In some embodiments, this diameter of the self-expanding funnel can be less than or equal to a diameter 1716 of the elongate member 106.

The self-expanding funnel 1708 can comprise a variety of shapes and sizes and can be made from a variety of materials. In some embodiments, the self-expanding funnel 1708 can have a maximum diameter greater than and/or equal to the diameter of the self-expanded coring element 206 in full expansion, and in some embodiments, the self-expanding funnel 1708 can have a minimum diameter equal to the diameter 1716 of the elongate member 106 and/or to the diameter of the lumen 1701 of the elongate member 106. In some embodiments, the self-expanding funnel 1708 can have a length greater than and/or equal to the length of the self-expanding coring element 206 such that the self-expanding coring element 206 can be received and contained within the self-expanding funnel 1708.

In some embodiments, the self-expanding funnel 1708 can have a conically shaped portion, and specifically, a truncated-conically shaped portion. In some embodiments, the self-expanding funnel can be formed from at least one of a castellated nitinol braid, a nitinol braided stent, a laser cut nitinol, a laser cut polymer tube, an injection molded polymeric structure, or an inflatable balloon. In some embodiments, the self-expanding funnel 1708 can comprise a mesh having a pore size sufficiently small to prevent the passage of dangerous thrombus through the pores of the mesh. In some embodiments, the self-expanding funnel 1708 can be permeable to blood.

With reference now to FIGS. 18 through 20, side views of embodiments of the introducer sheath 102 in different configurations are shown. In FIG. 18 the introducer sheath 102 is shown in an undeployed configuration, in FIG. 19, the introducer sheath 102 is shown in a partially deployed configuration, and in FIG. 20, the introducer sheath 102 is shown in a fully deployed and/or deployed configuration.

Specifically, as seen in FIG. 18, the obturator 120 extends through the lumen 1701 of the elongate member 106 and the self-expanding funnel 1708 is contained in a constrained configuration within the capture sheath 1500. In FIG. 19, the obturator 120 has been distally advanced to thereby release the self-expanding funnel 1708 from the constrained configuration and/or to deploy the self-expanding funnel 1708. In some embodiments, the length of the obturator 120, and specifically the length of the elongate shaft between the proximal end of the capture sheath 1500 and the stop portion 1508 is sufficient to allow the deployment of the self-expanding funnel 1708 from the capture sheath 1500 before further distal movement of the obturator 120 is prevented by the collision of the stop portion 1508 with the sealed aperture 112.

After the self-expanding funnel 1708 has been deployed, the obturator 120 can be proximally retracted through the lumen 1701 of the elongate member 106 and the sealed aperture 112 and can be removed from the introducer sheath 102. After the obturator 120 has been removed from the introducer sheath 102, the introducer sheath is in the fully deployed configuration as shown in FIG. 20.

Figure 21:
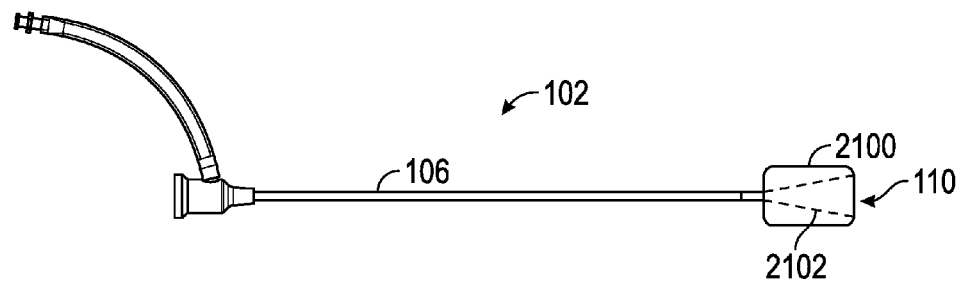
FIG. 21 is a side view of one embodiment of an introducer sheath comprising an inflatable balloon.

In some embodiments, and as seen in FIG. 21, the introducer sheath 102 can include an inflatable balloon 2100 located at, or proximate to the distal end 110 of the elongate member 106. In some embodiments, the balloon 2100 can comprise a conically shaped internal portion 2102 that can be sized and shaped to receive the thrombus extraction device 202, and specifically that can have a length greater than or equal to the length of the self-expanding coring element 206.

Figure 22:
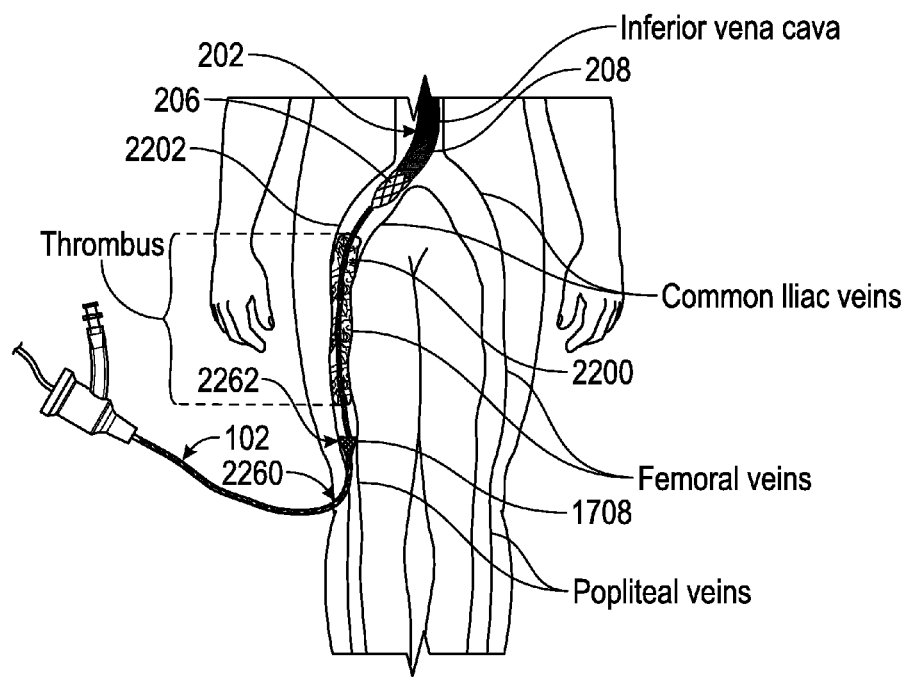
FIG. 22 is a schematic depiction of one embodiment of accessing the blood vessel via a popliteal access site.

With reference now to FIG. 22, an introduction technique for accessing the thrombus 2200 is shown. As depicted, the thrombus 2200 can be located in a blood vessel and accessed through an access site 2260 such as the popliteal access site. The introducer sheath 102 can extend from the popliteal access site 2260 to the deployment position 2262 at which the self-expanding funnel 1708 can be deployed and which can be proximate to the thrombus 2200. The TED 202 can be passed through the clot 2200 in the direction of blood flow and the TED 202 can be retracted through the clot 2200 in a direction opposite blood flow. The retraction of the TED 202 through the clot 2200 can result in the coring of the clot with the self-expanding coring element 206 and the capturing of the clot in the expandable cylindrical 208.

In some such embodiments, all or portions of the TED 202 can extend into one of the iliac veins and/or the inferior vena cava as depicted in FIG. 23. Further, as the TED 202 is retracted from a proximal position with respect to the heart to a distal position with respect to the heart, the diameter of the blood vessel 2202 will decrease as the TED 202 is retracted towards the access site 2260. This can result in increased compressive forces on the TED 202, and specifically on the self-expanding coring element 206. These compressive forces can be transferred via the ring feature 700 and the stop 702 to the compliance spring 1214. Via the stretching or compressing of the compliance spring 1214, the diameter of the TED 202 and specifically of the coring element 206 can change to match the diameter of the blood vessel and a desired radial force, and/or force level can be maintained.

FIGS. 23-A to 23-H, FIGS. 24-A and 24-B, and FIGS. 25-A to 25-H depict processes for using the thrombus extraction system 100 to remove thrombus from a patient's body, and specifically from a blood vessel, which can be a venous vessel, in the patient's body. This includes: accessing the blood vessel via one or several percutaneous access sites that can provide direct access to the blood vessel or indirect access to the blood vessel via one or several other blood vessels; advancing the introducer sheath to a position proximate to the thrombus; deploying the self-expanding funnel of the introducer sheath; advancing the distal end 132 of the thrombus extraction catheter 104 to a position proximate to the thrombus; deploying the thrombus extraction device 202; capturing the thrombus in the thrombus extraction device 202 by retracting the thrombus extraction device 202 through the thrombus; collapsing the thrombus extraction device 202; and removing the thrombus extraction device 202 and the captured thrombus from the introducer sheath 102 and from the patient's body. In some embodiments, these one or several access sites can include, for example, a popliteal access site, a femoral access site, and/or an internal jugular access site. In some embodiments, a thrombolytic agent can be infused and/or aspirated into or from the blood vessel before, during, or after the removal or extraction of the thrombus The process for using the thrombus extraction system 100 shown in FIGS. 22-A to 22-H, FIGS. 24-A and 24-B, and FIGS. 25-A to 25-H can be performed with the direction of blood flow or against the direction of blood flow. Thus, in some embodiments, the direction of blood flow in FIGS. 22-A to 22-H, FIGS. 24-A and 24-B, and FIGS. 25-A to 25-H, can be from left to right, or from right to left.

With reference now to FIGS. 23-A to 23-H, a process for expanding the thrombus extraction device 202 in a blood vessel such as a venous vessel is shown. The process for expanding the thrombus extraction device 202 in the vessel can be performed using all or portions of the thrombus extraction system 100. In some embodiments, the process for expanding the thrombus extraction device 202 in the vessel can be performed in connection with a monitoring technique, such as fluoroscopy, angiography, and/or ultrasonic monitoring. In some embodiments, the monitoring technique can be used to monitor the deployment of the TED 202 in the vessel via observation of the one or several radiopaque markers located on the introducer sheath 102 and/or the thrombus extraction catheter 104.

The process begins at FIG. 23-A, wherein a thrombus 2200 is identified in a blood vessel 2202 such as venous vessel. In some embodiments, the thrombus 2200 can be located in the peripheral vasculature of the patient's body. The thrombus 2200, also referred to herein as a clot 2200, can comprise a proximal end 2204 and the distal end 2206. In some embodiments, the identification of the blood vessel 2202 can further include the determination of whether the thrombus 2200 in the blood vessel 2202 is suitable for thrombus extraction. In some embodiments, the thrombus 2200 in the blood vessel 2202 can be suitable for extraction when the blood vessel 2202 has a diameter of at least 5 millimeters. In some embodiments, the thrombus 2200 in the blood vessel 2202 can be suitable for extraction when the blood vessel 2202 has a diameter of at least 5 millimeters and is at least one of a femoral vein, an iliac vein, a popliteal vein, a posterior tibial vein, an anterior tibial vein, or a peroneal vein.

After the thrombus has been identified, the process proceeds to the step shown in FIG. 23-B, wherein the introducer sheath 102 is advanced, either with or against the direction of blood flow in the blood vessel, such that the distal end 110 of the introducer sheath 102 and/or the obturator 120 is proximate to the thrombus 2200, and particularly is proximate to the thrombus 2200 at a position proximal of the thrombus 2200. In some embodiments, this can include providing the introducer sheath 102 and percutaneously accessing the circulatory system of the patient and specifically a blood vessel or venous vessel of the patient via an access site 2208 which can be one of the above referenced access sites.

After the introducer sheath 102 has been advanced to a desired position, the self-expanding funnel 1708 can be deployed and/or unsheathed from the constrained configuration to the expanded configuration as depicted in FIG. 23-C. In some embodiments, the self-expanding funnel 1708 can be deployed by the relative distal movement of the obturator 120 with respect to the elongate member 106 until the funnel 1708 is no longer constrained by the capture sheath 1500 and then the obturator 120 can be proximally retracted through the lumen 1701 of the elongate member 106 until the obturator 120 is removed from the introducer sheath 102.

In some embodiments, the relative distal movement of the obturator 120 with respect to the elongate member can comprise fixing the position of the obturator 120 relative to the blood vessel 2202 and proximally retracting the elongate member 106 over the obturator 120 to unsheathe the self-expanding funnel 1708 until the stop 1508 contacts the sealed aperture 112 and/or until monitoring, which can be fluoroscopic monitoring, of radiopaque markers located in, for example, the tip 1502 of the obturator 120 and the distal end 110 of the elongate member 106 indicate that the self-expanding funnel 1708 is deployed and/or is no longer constrained by the capture sheath 1500. Alternatively, in some embodiments, the relative distal movement of the obturator 120 with respect to the elongate member can comprise fixing the position of the elongate member 106 relative to the blood vessel 2202 and distally advancing the obturator 120 two unsheathe the self-expanding funnel 1708 until the stop 1508 contacts the sealed aperture 112 and/or until monitoring, which can be fluoroscopic monitoring, of radiopaque markers located in, for example, the tip 1502 of the obturator 120 and the distal end 110 of the elongate member 106 indicate that the self-expanding funnel 1708 is deployed and/or is no longer constrained by the capture sheath 1500.

After the self-expanding funnel 1708 has been deployed, a portion of the thrombus extraction catheter 104 such as the outer shaft 138 can be inserted into the lumen 1701 of the introducer sheath 102 via the sealed aperture 112 as depicted in FIG. 23-D. In some embodiments, this can include providing the thrombus extraction catheter 104 which comprises the thrombus extraction device 202. In some embodiments, the thrombus extraction device 202 can be constrained within the outer shaft 138 and can inserted, together with the outer shaft 138, into the lumen of the elongate member 106 via the sealed aperture 112. In some embodiments, the outer shaft 138 of the thrombus extraction catheter 104 can have a diameter so as to dilate the seal of the sealed aperture 112 such that the sealed aperture 112 seals around and seals to the outer shaft 138.

After the outer shaft 138 has been inserted into the lumen 1701 of the introducer sheath 102, a portion of the thrombus extraction catheter 104 can be inserted via the introducer sheath 102 into the blood vessel 2202 as depicted in FIG. 23-E. In some embodiments, the distal end 132 of the thrombus extraction catheter 104 can be advanced to a position proximate to the thrombus 2200 and/or to a position proximal to the thrombus 2200. In some embodiments, the insertion and/or advance of the thrombus extraction catheter 104 can be monitored and specifically can be fluoroscopically monitored. In some embodiments, the position of one or several radiopaque markers, including radiopaque marker 222 of the thrombus extraction catheter 104 can be monitored.

After the portion of the thrombus extraction catheter 104 has been inserted into the blood vessel 2202, a portion of the thrombus extraction catheter 104 can be distally advanced through the clot 2200 as depicted in FIG. 23-F. In some embodiments, this distal advance through the clot 2200 can be either with or against the direction of blood flow. In some embodiments, the portion of the thrombus extraction catheter 104 distally advanced through the clot 2000 can contain and/or constrain the thrombus extraction device 202. In some embodiments, distally advancing the portion of the thrombus extraction catheter 104 through the clot can include advancing the portion of the thrombus extraction catheter 104 until the radiopaque marker 222, that can be fluoroscopically monitored and that can be located at the distal end 218 of the inner shaft 200, is distally past the thrombus 2200 and/or a portion of the thrombus 2200.

After the portion of the thrombus extraction catheter 104 is distally advanced through the clot 2200, the thrombus extraction device 202 can be deployed as depicted in FIG. 23-G. In some embodiments, the thrombus extraction device 202 can be deployed by either advancing the thrombus extraction device 202 beyond the distal end 204 of the outer shaft 138 or by retracting the outer shaft 138 relative to the thrombus extraction device 202 until the thrombus extraction device 202 is beyond the distal end 204 of the outer shaft 138. In some embodiments, the thrombus extraction device can be deployed such that the thrombus extraction device 202 is distally past the thrombus 2200 and/or distally past a desired portion of the thrombus 2200.

In some embodiments, the thrombus extraction device is advanced beyond the distal end 204 of the outer shaft 138 by distally advancing the intermediate shaft 140 with respect to the outer shaft 138. In some embodiments, the intermediate shaft 140 can be distally advanced until the lock feature 146 contacts the mating feature 148, and the lock feature 146 can be mated and/or secured to the mating feature 148 to fix the relative position of the intermediate shaft 140 with respect to the outer shaft 138.

In some embodiments, the deployment of the thrombus extraction device 202 can be monitored, and specifically, the deployment of the thrombus extraction device 202 can be fluoroscopically monitored via, for example, the radiopaque marker 222 and the radiopaque marker located at one or both of the distal end 204 of the outer sheath 138 and the distal end 212 of the intermediate sheath 140. In some embodiments, the deployment of the thrombus extraction device 202, and specifically the advancing of the thrombus extraction device 202 beyond the distal end 204 of the outer shaft 138 or retracting the outer shaft 138 relative to the thrombus extraction device 202 can be ceased based on a position the distal end 204 of the outer sheath 138 comprising the radiopaque marker (first radiopaque marker) relative to the radiopaque marker 222 located on the thrombus extraction device 202 (second radiopaque marker).

After the thrombus extraction device 202 is deployed, the thrombus extraction device 202 can be fully expanded as shown in FIG. 23-H. In some embodiments, this can include allowing the full expansion of the thrombus extraction device 202 such that the thrombus extraction device 202 engages a wall 2220 of the blood vessel 2202. In some embodiments, the thrombus extraction device 202 can be fully expanded by moving the plunger 154 from the first position to the second position and securing the plunger 154 in the second position to thereby fix the relative position of the inner shaft 200 with respect to the intermediate shaft 140. In some embodiments, the movement of the plunger 154 from the first position to the second position proximally retracts the inner shaft 200 with respect to the intermediate shaft 140 to thereby fully expand the expandable cylindrical portion 208 of the thrombus extraction device 202. The proximal retraction of the inner shaft 200 with respect to the intermediate shaft 140 can further bring the stop 702 into engagement with the ring feature 700 to thereby fully expand the self-expanding coring element 206. In some embodiments, the securing of the plunger 154 in the second position can secure the self-expanding coring element 206 and the thrombus extraction device 202 in full expansion via the engagement of the stop 702 with the ring feature 700.

With reference now to FIGS. 24-A and 24-B, alternative embodiments of the steps shown in FIGS. 23-G and 23-H are shown. In some embodiments, these alternative embodiments can be performed when the diameter of the blood vessel 2202 containing the thrombus 2200 decreases below a desired level distally beyond the thrombus 2200. In some embodiments, for example, as the distance from the heart increases, the diameter of the blood vessel 2202 can decrease. In some embodiments, this diameter can decrease to a point that use of the thrombus extraction device 202 may no longer be possible.

In such an embodiment, an extension sheath 2300, also referred to herein as a popliteal sheath 2300, can be percutaneously inserted into the blood vessel 2202 through the wall 2220 of the blood vessel 2202 such that at least a portion of the extension sheath 2300 extends from the patient. In some embodiments, the extension sheath 2300 can be percutaneously inserted into the blood vessel 2202 at a position before the blood vessel diameter decreases below a desired value such as, for example, below 1 mm, 2 mm, 3 mm, 4 mm, 5 mm, 6 mm, 8 mm, 10 mm, or any other or intermediate value. In some embodiments the extension sheath 2300 can be inserted into the blood vessel 2202 via an access site such as, for example, the popliteal access site.

The thrombus extraction device 202 can be deployed as depicted in FIG. 24-A. In some embodiments, the thrombus extraction device 202 can be deployed by either advancing the thrombus extraction device 202 beyond the distal end 204 of the outer shaft 138 and into the extension sheath 2300 or by advancing the outer shaft 138 containing the thrombus extraction device 202 into the extension sheath and then retracting the outer shaft 138 relative to the thrombus extraction device 202 until the thrombus extraction device 202 is beyond the distal end 204 of the outer shaft 138. In some embodiments, the thrombus extraction device can be deployed such that the thrombus extraction device 202 is distally past the thrombus 2200 and/or distally past a desired portion of the thrombus 2200. In some embodiments, all or portions of the thrombus extraction device can be contained within the extension sheath 2300.

In some embodiments, the outer shaft 138 of the thrombus extraction catheter 104 can be separable into a first piece and a second piece. In some embodiments, this separation can occur at a separation point that can comprise, for example, any feature configured to allow separation of the first and second pieces. These features can include a partial depth slit or score in the outer shaft 138, an overlapping friction fit in the outer shaft 138, or the like. In some embodiments, the separable outer shaft 138 can be used in the place of the extension sheath 2300. In such an embodiment, the outer shaft 138 can exit the blood vessel 2202 via the access site such that the separable portion extends from inside the blood vessel 2202 to outside of the patient's body at the access point. In such an embodiment, the separation portion of the outer sheath 138 can serve as the extension sheath 2300 and can remain in the access point when the thrombus extraction device 202 is retracted. Thus, the thrombus extraction device 202 can be deployed by securing the position of the separation portion of the outer sheath 138 and retracting the thrombus extraction device 202 from that separation portion of the outer sheath 138.

In some embodiments, the thrombus extraction device can be advanced beyond the distal end 204 of the outer shaft 138 by distally advancing the intermediate shaft 140 with respect to the outer shaft 138. In some embodiments, the intermediate shaft 140 can be distally advanced until the lock feature 146 contacts the mating feature 148. In some embodiments, the lock feature 146 can be mated and/or secured to the mating feature 148 to fix the relative position of the intermediate shaft 140 with respect to the outer shaft 138.

In some embodiments, the deployment of the thrombus extraction device 202 can be fluoroscopically monitored, and specifically, the deployment of the thrombus extraction device 202 can be fluoroscopically monitored via, for example, the radiopaque marker 222 and the radiopaque marker located at one or both of the distal end 204 of the outer sheath 138 and the distal end 212 of the intermediate sheath 140. In some embodiments, the deployment of the thrombus extraction device 202, and specifically the advancing of the thrombus extraction device 202 beyond the distal end 204 of the outer shaft 138 or retracting the outer shaft 138 relative to the thrombus extraction device 202 can be seized based on a position the distal end 204 of the outer sheath 138 comprising the radiopaque marker (first radiopaque marker) relative to the radiopaque marker 222 located on the thrombus extraction device 202 (second radiopaque marker).

After the thrombus extraction device 202 is deployed, the thrombus extraction device 202 can be fully expanded as shown in FIG. 24-B. in some embodiments, the thrombus extraction device 202 can be fully expanded while all or portions of the thrombus extraction device 202 are contained in the extension sheath 2300. In such an embodiment, the portions of the thrombus extraction device 202 contained in the extension sheath 2300 can be prevented from reaching full expansion by the extension sheath 2300. In such an embodiment, the thrombus extraction device 202 can reach full expansion as the thrombus extraction device is proximately retrieved from the extension sheath 2300.

In some embodiments, the full expansion of the thrombus extraction device 202 can include allowing the expansion of the thrombus extraction device 202 such that the thrombus extraction device 202 engages a wall 2220 of the blood vessel 2202. In some embodiments, the thrombus extraction device 202 can be fully expanded by moving the plunger 154 from the first position to the second position and securing the plunger 154 in the second position to thereby fix the relative position of the inner shaft 200 with respect to the intermediate shaft 140. The movement of the plunger 154 from the first position to the second position can proximally retract the inner shaft 200 with respect to the intermediate shaft 140 to thereby expand the expandable cylindrical portion 208 of the thrombus extraction device 202. In some embodiments, the proximal retraction of the inner shaft 200 with respect to the intermediate shaft 140 can further bring the stop 702 into engagement with the ring feature 700 to thereby fully expand the self-expanding coring element 206. In some embodiments, the securing of the plunger 154 in the second position can secure the self-expanding coring element 206 and the thrombus extraction device 202 in full expansion via the engagement of the stop 702 with the ring feature 700

In some such embodiments in which the TED 202 is all or wholly contained within the extension sheath 2300, the TED 202 can be retracted until the self-expanding coring element 206 is outside of the extension sheath 2300, and which point the inner shaft 200 can be decoupled from the distal end 217 of the expandable cylindrical portion 208 and the plunger 154 can be moved from the first position to the second position to bring the self-expanding coring element 206 to full expansion. The TED 202 can then be further retracted and the expandable cylindrical portion 208 can be expanded by progressively recoupling the distal end 217 of the expandable cylindrical portion 208 with the inner shaft 200 as the expandable cylindrical portion 208 exits the extension sheath 2300 until the expandable cylindrical portion 208 has completely exited the extension sheath 2300 and is at full expansion with the distal end 217 of the expandable cylindrical portion 208 recoupled to the inner shaft 140. Alternatively, in some embodiments, the distal end 217 of the expandable cylindrical portion 208 can remain uncoupled to the inner shaft 140 until the expandable cylindrical portion 208 has completely exited the extension sheath 2300. Once the expandable cylindrical portion 208 has completely exited the extension sheath 2300, the distal end 217 of the expandable cylindrical portion 208 can be recoupled to the inner shaft 200 and the expandable cylindrical portion 208 can be expanded to full expansion.

With reference now to FIGS. 25-A to 25-H a process for removal of thrombus 2200 with an expanded thrombus extraction device 202 is shown. In some embodiments, the thrombus 2200 can be removed via the capture of the thrombus in the thrombus extraction device 202 via the proximal retraction of the thrombus extraction device 202 through the thrombus 2200, which proximal retraction of the thrombus extraction device 202 can be, for example, in a direction of blood flow through the blood vessel 2202 or against the direction of blood flow through the vessel 2202. In some embodiments, the proximal retraction of the thrombus extraction device 202 through the thrombus 2200 can result in the capture of the distal end 2206 of the thrombus 2200 before the capture of the proximal end 2204 of the thrombus 2200.

In some embodiments, the proximal retraction of the thrombus extraction device 202 can result in the separation and/or coring of at least a portion of the thrombus 2200 from the wall 2220 of the blood vessel 2202 by, for example, the self-expanding coring element 206 and/or the stent portion, and the capture of that separated portion of the thrombus 2200 within the expandable cylindrical portion 208. In some embodiments, the expandable cylindrical portion 208 can be formed of the braided filament mesh structure that can be, for example, a net-like filament mesh structure. In some embodiments, a portion of the thrombus can be captured within the expandable cylindrical portion 208 by entering the expandable cylindrical portion 208 via the mouth 414 of the self-expanding coring element 206 and/or via one or several of the interstices 404 of the self-expanding coring element 206.

As seen in FIG. 25-A, the distal end 2206 of the thrombus 2200 is separated and/or cored from the walls 2220 of the blood vessel 2202 by the self-expanding coring element 206 via the proximal retraction of the thrombus extraction device 202. As seen in FIG. 25-B, the distal end 2206 of the thrombus 2200 is captured in the expandable cylindrical portion 208 of the thrombus extraction device by the continued proximal retraction of the thrombus extraction device through the thrombus 2200. The separation and capture and/or coring and capture of further portions of the thrombus 2200 by the continued proximal retraction of the thrombus extraction device 202 is shown in FIGS. 25-C, 25-D, and 25-E. As seen in FIG. 25-E, the proximal end 2204 of the thrombus 2200 is cored and captured as the thrombus extraction device 202 is proximally retracted towards the self-expanding funnel 1708.

In some embodiments, the thrombus extraction device 202 can be proximally retracted until a portion of the self-expanding coring element 206 is contained within the self-expanding funnel 1708 as seen in FIG. 25-F, and specifically until the mouth 414 of the self-expanding coring element 206 is contained within the self-expanding funnel 1708. In some embodiments, the containment of the mouth 414 within the self-expanding funnel 1708 can be fluoroscopically verified. In some embodiments, the mouth 414 can be determined as wholly contained within the self-expanding funnel 1708 via fluoroscopic monitoring based on the alignment/relative positioning of the distal end 212 of the intermediate shaft 140 comprising a radiopaque marker 2450 and/or the radiopaque marker 222 with respect to the distal end 110 comprising a radiopaque marker 2452 of the elongate member 106 of the introducer sheath 102.

When the portion of the self-expanding coring element 206 is contained within the self-expanding funnel 1708, or specifically when the mouth 414 of the self-expanding coring element 206 is wholly contained within the self-expanding funnel 1708, the plunger 154 can be unlocked from the second position and can be moved from the second position to the first position to thereby move the thrombus extraction device 202 from and expanded configuration to an unexpanded configuration. In some embodiments, the unlocking of the plunger 154 from the second position can unlock and/or decouple the inner shaft 200 with respect to the intermediate shaft 140, and the moving of the plunger 154 from the second position to the first position can cause the distal advancing of the inner shaft 200 relative to the intermediate shaft 140.

In some embodiments, the thrombus extraction device 202 can be collapsed by moving the thrombus extraction device 202 from the expanded configuration to the unexpanded configuration prior to withdrawing the thrombus extraction device 202 from the patient's body so as to compress the thrombus 2200 captured by the thrombus extraction device 202. In some embodiments, the compression of the thrombus 2200 by the thrombus extraction device 202 can secure the position of the thrombus within the thrombus extraction device 202 via, in some embodiments, the engagement of one or several of the plurality of circumferential depressions 1000 with the thrombus 2200.

After the thrombus extraction device 202 has been collapsed, the thrombus extraction device 202 can be proximally retracted through the self-expanding funnel 1708 and into the elongate member 106 as depicted in FIG. 25-G. In some embodiments, the collapse of the thrombus extraction device 202 and/or the retraction of the thrombus extraction device 202 into the self-expanding funnel 1708 and/or the elongate member can result in the extrusion of all or portions of the thrombus 2200 through pores of the expandable cylindrical portion 208 of the thrombus extraction device 202 including, for example, some or all of the first plurality of pores 904 and/or the second plurality of pores 906. In some embodiments, the all or portions of the thrombus 2200 can be extruded through some or all of the second plurality of pores 906 which can be larger than the first plurality of pores 904. In some embodiments, the pores in the second plurality of pores 906 can be sized to be sufficiently small such that any thrombus portions of the thrombus 2200 extruded through the pores is sufficiently small to have little or no clinical significance. In some embodiments, these extruded all or portions of the thrombus 2200 can be captured by the self-expanding funnel 1708.

The thrombus extraction device 202 can continue to be proximally retracted as depicted in FIG. 25-H until the thrombus extraction device 202 and the captured thrombus 2200 is fully contained within the elongate member 106. In some embodiments, the seal dilator 170 can be inserted into the sealed aperture 112 and the thrombus extraction device 202 and the captured thrombus 2200 can then be withdrawn or removed from the patient's body and from the elongate member 106 via the sealed aperture 112 in the seal dilator 170. In some embodiments, thrombus captured by the self-expanding funnel 1708 can then either be guided into the elongate member 106 and specifically into the lumen 1701 of the elongate member 106 or further compressed and/or broken up by the self-expanding funnel 1708 and then allowed to pass through the self-expanding funnel 1708, and particularly through the mesh of the self-expanding funnel 1708. In some embodiments, this thrombus can be aspirated through the lumen 1701 of the elongate member 106 and the aspiration port 114. In some embodiments, the aspiration of the thrombus via the aspiration port 114 can include the opening of the aspiration valve 118. After the thrombus is captured by the self-expanding funnel 1708 has been aspirated, the introducer sheath 102 can be removed from the patient's body.

Figure 26:
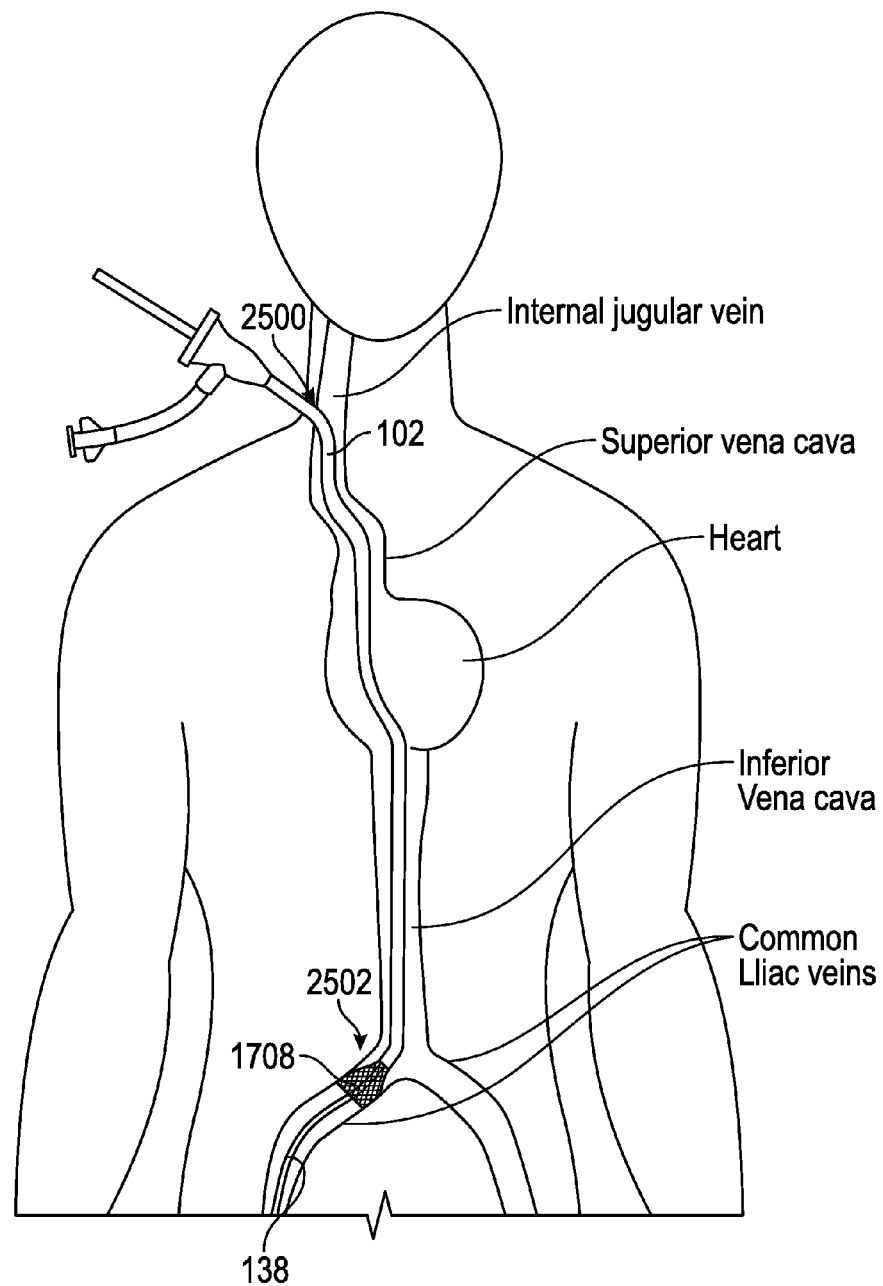
FIG. 26 is a schematic depiction of one embodiment of accessing the blood vessel via an internal jugular access site.
Figure 27:
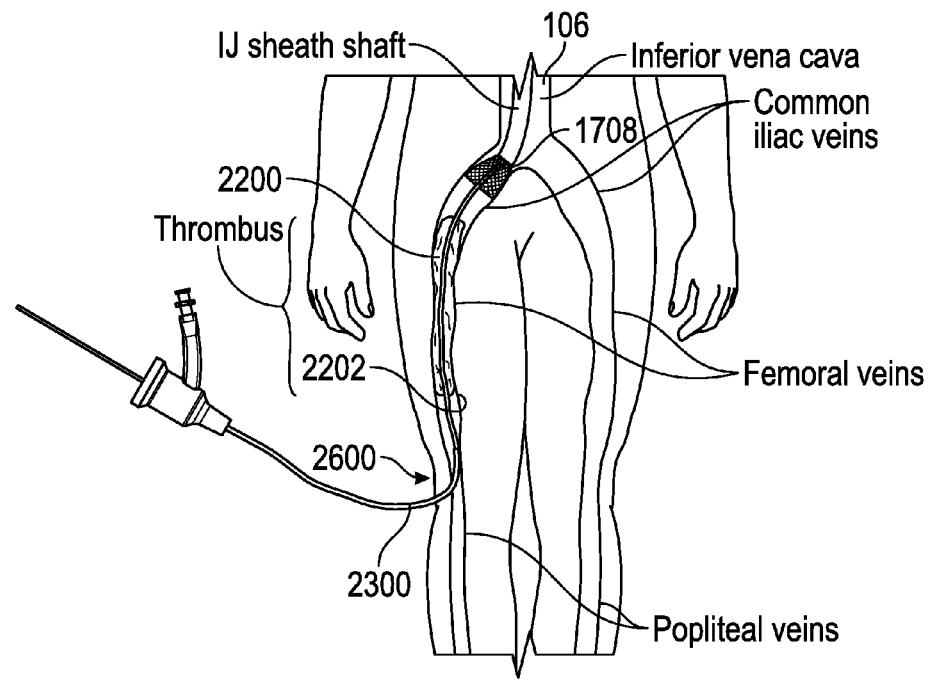
FIG. 27 is a schematic depiction of one embodiment of accessing the blood vessel via a popliteal access site with an extension sheath 2300.
Figure 28:
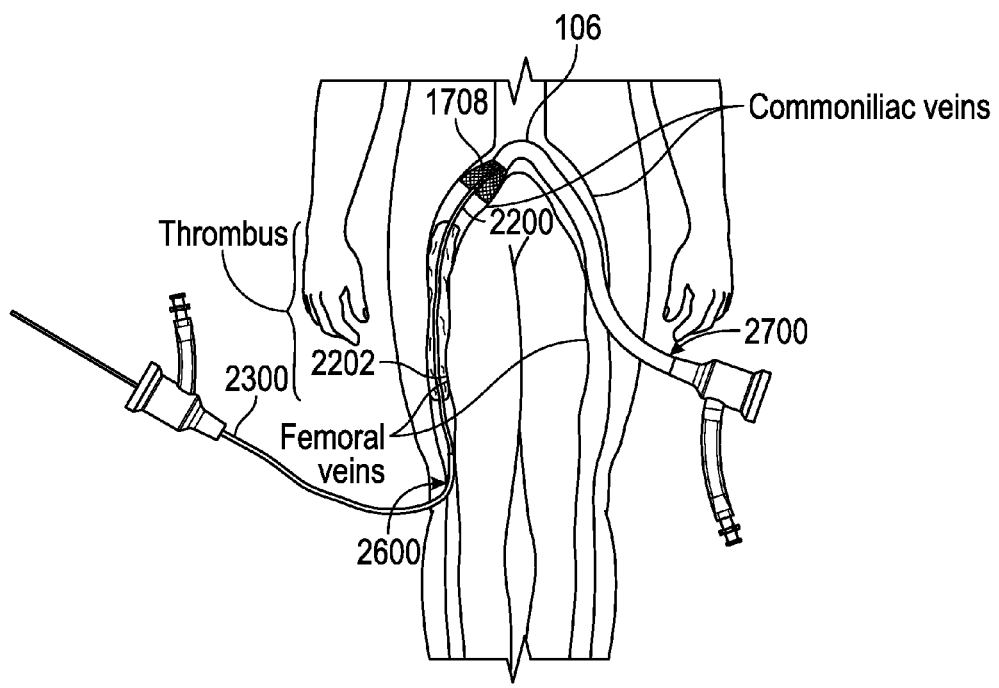
FIG. 28 is a schematic depiction of one embodiment of accessing the blood vessel via a popliteal access site and a femoral access site.

With reference now to FIGS. 26-28, introduction techniques for accessing the thrombus 2200 are shown. In some embodiments, these introduction techniques can allow the use of a larger sized introducer sheath 102 due to the larger size of the vessels in the path to the thrombus. In some embodiments, this larger size of the introducer sheath 102 can ease the removal of thrombus through the introducer sheath 102 as, in some embodiments, the size of the lumen 1701 of the introducer sheath 102 can increase as the size of the introducer sheath 102 increases. Further, in some embodiments, the user of a larger sized introducer sheath 102 can allow the removal of larger thrombus. In some embodiments, the lengths of the components of the thrombus extraction system 100, and particularly the lengths of the introducer sheath 102 and the thrombus extraction catheter 104 can vary based on the selected technique for accessing the thrombus and/or based on the location of the thrombus.

As seen in FIG. 26, the introducer sheath 102 can be inserted into the patient's body via an internal jugular access site 2500. The introducer sheath 102 can extend from the internal jugular access site 2500 to the deployment position 2502 which can be proximal to the thrombus 2200. In embodiments in which the introducer sheath 102 comprises the self-expanding funnel 1708, the self-expanding funnel 1708 can be deployed at the deployment position 2502. In the embodiment shown in FIG. 26, the introducer sheath can extend from the internal jugular access site 2500 through the superior vena cava and the inferior vena cava to the deployment position 2502 in one of the common iliac veins. In some embodiments, the deployment position 2502 can be located in, for example, the inferior vena cava, one of the iliac veins, the femoral vein, the popliteal vein, before or beyond the iliac arch, or any other location proximate to and/or proximal to the thrombus 2200. In some embodiments, the use of the internal jugular access site 2500 can allow for a larger diameter of the elongate member 106.

As seen in FIG. 27, in some embodiments, use of the internal jugular access site 2500 can be combined with use of the extension sheath 2300 that can be inserted into the blood vessel 2202 at a popliteal access site 2600. In some such embodiments, the thrombus extraction device can wholly or partially exit the patient's body while contained in the extension sheath 2300 before being retracted through the thrombus 2200.

As seen in FIG. 28, the introducer sheath can, in some embodiments, be inserted into the patient's body into an access site connected to the blood vessel 2202 containing the thrombus via the common iliac veins. In the specific embodiment shown in FIG. 28, this can be achieved via insertion into the patient's body via a femoral access site 2700. In some embodiments, use of an access site connected to the blood vessel 2202 via the common iliac veins, and specifically user of the femoral access site 2700 can be combined with user of the extension sheath 2300 that can be inserted into the blood vessel 2202 at a popliteal access site 2600. In some such embodiments, the thrombus extraction device can wholly or partially exit the patient's body while contained in the extension sheath 2300 before being retracted through the thrombus 2200.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

In the previous description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of treating deep vein thrombosis in a peripheral vasculature of a patient, the method comprising:
   providing a thrombus extraction device comprising a proximal self-expanding coring portion and a distal expandable tubular portion formed of a filament mesh structure, wherein the mesh structure filaments are interwoven with the coring portion so that a proximal end of the mesh structure is attached to a distal end of the coring portion;
   advancing a catheter constraining the thrombus extraction device through a vascular thrombus in a venous vessel, wherein an intermediate shaft slidably extends through the catheter and a distal end thereof is coupled to a proximal end of the coring portion, and wherein an inner shaft slidably extends through the intermediate shaft and a distal end thereof is coupled to a distal end of the mesh structure;
   deploying the thrombus extraction device from the catheter from a constrained configuration to an expanded configuration, wherein the thrombus extraction device in an expanded state engages at least a wall of the vessel distally past a portion of the vascular thrombus;
   retracting the thrombus extraction device proximally so that the coring portion cores and separates a portion of the vascular thrombus from the venous vessel wall while the mesh structure captures the vascular thrombus portion; and
   withdrawing the thrombus extraction device from the patient to remove the vascular thrombus portion from the venous vessel.

2. The method of claim 1, wherein advancing the catheter comprises inserting the catheter into the venous vessel until a radiopaque distal tip of the catheter is distally past the vascular thrombus portion.

3. The method of claim 1, wherein deploying the thrombus extraction device from the catheter from the constrained configuration to the expanded configuration comprises advancing the intermediate shaft distally until the coring portion of the thrombus extraction device is beyond a distal end of the catheter.

4. The method of claim 3, wherein deploying the thrombus extraction device further comprises:
locking the intermediate shaft with respect to the catheter;
retracting the inner shaft with respect to the catheter and the intermediate shaft until a stop feature fixed on the inner shaft engages a corresponding feature on the coring portion slidably connected to the inner shaft for expansion of the thrombus extraction device, wherein the coring portion has a coring angle in a range between about 30 degrees and about 45 degrees when the thrombus extraction device is in the expanded state, wherein the coring portion maintains sufficient radial force on the venous vessel wall to core and separate the vascular thrombus portion in the expanded state; and
dynamically coupling the inner shaft with respect to the intermediate shaft.

5. The method of claim 3, wherein deploying the thrombus extraction device further comprises determining a position of the thrombus extraction device with respect to the catheter via imaging of a first radiopaque marker located on the catheter and a second radiopaque marker located on at least one of the intermediate shaft, the inner shaft, coring portion, or mesh structure.

6. The method of claim 1, wherein the vascular thrombus portion is captured into the mesh structure by entering the expandable tubular portion via at least one proximal opening or aperture located at the proximal end of the self-expanding coring portion.

7. The method of claim 1, further comprising inserting the catheter into the venous vessel through an access site, wherein the access site comprises a popliteal access site, a femoral access site, or an internal jugular access site.

8. The method of claim 1, wherein the venous vessel has a diameter of at least 5 millimeters and comprises at least one of a femoral vein, an iliac vein, a popliteal vein, a posterior tibial vein, an anterior tibial vein, or a peroneal vein.

9. The method of claim 1, further comprising:
percutaneously accessing the venous vessel of the patient with an introducer sheath through an access site into the venous vessel of the patient;
advancing a distal end of the introducer sheath to a position proximal of the vascular thrombus;
deploying a self-expanding funnel on the distal end of the introducer sheath; and
inserting the catheter through a lumen of the introducer sheath so that a distal tip of the catheter is distally past the vascular thrombus portion.

10. The method of claim 9, wherein deploying the self-expanding funnel comprises:
advancing an obturator having a capture sheath feature on a distal end thereof to unsheathe the self-expanding funnel from a constrained configuration within the capture sheath feature to a deployed configuration free of the capture sheath feature; and
removing the obturator from the introducer sheath by retracting the obturator through the deployed self-expanding funnel and through the lumen of the introducer sheath.

11. The method of claim 9, wherein withdrawing the thrombus extraction device from the patient comprises:
retracting the thrombus extraction device relative to the introducer sheath until a proximal opening of the self-expanding coring portion is within the self-expanding funnel;
collapsing the coring portion and mesh structure so as to restrain and/or compress the vascular thrombus portion therein;
retracting the coring portion and mesh structure into the introducer sheath; and
removing the thrombus extraction device from the introducer sheath.

12. The method of claim 11, further comprising extruding at least one piece of the vascular thrombus portion through pores located at a distal portion of the expandable tubular portion and capturing the at least one piece of the vascular thrombus portion in the self-expanding funnel or further compressing the at least one piece of the vascular thrombus portion through a mesh of the self-expanding funnel.

13. The method of claim 11, further comprising aspirating at least one piece of the vascular thrombus portion remaining within the self-expanding funnel from the venous vessel and through an aspiration port connected to a proximal end of the introducer sheath.

14. The method of claim 11, further comprising verifying that the proximal opening of the self-expanding coring portion is within the self-expanding funnel via fluoroscopy prior to collapsing the coring portion and mesh structure.

15. The method of claim 11, wherein collapsing the coring portion and mesh structure comprises:
decoupling the inner shaft and the intermediate shaft; and
advancing the inner shaft distally relative to the intermediate shaft.

16. The method of claim 1, further comprising aspirating or infusing a thrombolytic agent into or from the venous vessel before, during, or after thrombus extraction.

17. A method of treating deep vein thrombosis in a peripheral vasculature of a patient, the method comprising:
percutaneously accessing a venous vessel of a patient with an introducer sheath through an access site into the venous vessel of the patient;
deploying a self-expanding funnel on a distal end of the introducer sheath proximal of a vascular thrombus, wherein deploying the self-expanding funnel comprises advancing an obturator having a capture sheath feature on a distal end thereof to unsheathe the self-expanding funnel from a constrained configuration within the capture sheath feature to a deployed configuration free of the capture sheath feature;
removing the obturator from the introducer sheath by retracting the obturator through the deployed self-expanding funnel and through a lumen of the introducer sheath
inserting a catheter constraining a thrombus extraction device through the lumen of the introducer sheath so that a distal tip of the catheter is distally past a portion of the vascular thrombus in the venous vessel, wherein the thrombus extraction device comprises a proximal self-expanding coring portion defining a coring angle and a distal expandable tubular portion formed of a mesh structure, wherein a proximal end of the mesh structure is coupled to a distal end of the coring portion;
deploying the thrombus extraction device from the catheter from a constrained configuration to an expanded configuration until the coring portion of the thrombus extraction device is beyond a distal end of the catheter, wherein the coring angle is in a range between about 20 degrees and about 50 degrees when the thrombus extraction device is in an expanded state;

retracting the thrombus extraction device proximally so that the coring portion cores and separates the portion of the vascular thrombus from a venous vessel wall while the mesh structure captures the vascular thrombus portion, wherein the coring portion maintains sufficient radial force on the venous vessel wall to core and separate the vascular thrombus portion in the expanded state; and withdrawing the thrombus extraction device from the patient.

18. The method of claim 17, wherein withdrawing the thrombus extraction device from the patient comprises:

retracting the thrombus extraction device relative to the introducer sheath until a proximal opening of the self-expanding coring portion is within the self-expanding funnel;

collapsing the coring portion and mesh structure so as to restrain and/or compress the vascular thrombus portion therein;

retracting the coring portion and mesh structure into the introducer sheath; and removing the thrombus extraction device from the introducer sheath.

19. The method of claim 18, further comprising extruding at least one piece of the vascular thrombus portion through pores located at a distal portion of the expandable tubular portion and capturing the at least one piece of the vascular thrombus portion in the self-expanding funnel or further compressing the at least one piece of the vascular thrombus portion through a mesh of the self-expanding funnel.

20. The method of claim 18, further comprising aspirating at least one piece of the vascular thrombus portion remaining within the self-expanding funnel from the venous vessel and through an aspiration port connected to a proximal end of the introducer sheath.

21. The method of claim 17, wherein the coring angle is in a range between about 30 degrees and about 45 degrees when the thrombus extraction device is in the expanded state.

22. The method of claim 17, wherein the vascular thrombus portion is captured into the mesh structure by entering the expandable tubular portion via at least one proximal opening or aperture located at the proximal end of the self-expanding coring portion.

23. A method of treating deep vein thrombosis in a peripheral vasculature of a patient, the method comprising:

percutaneously accessing a venous vessel of a patient with an introducer sheath through an access site into the venous vessel of the patient;

inserting a catheter constraining a thrombus extraction device through a lumen of the introducer sheath so that a distal tip of the catheter is distally past a portion of a vascular thrombus in the venous vessel, wherein the thrombus extraction device comprises a proximal self-expanding coring portion defining a coring angle and a distal expandable tubular portion formed of a mesh structure, wherein a proximal end of the mesh structure is coupled to a distal end of the coring portion;

deploying the thrombus extraction device from the catheter from a constrained configuration to an expanded configuration until the coring portion of the thrombus extraction device is beyond a distal end of the catheter, wherein the coring angle is in a range between about 20 degrees and about 50 degrees when the thrombus extraction device is in an expanded state, wherein deploying the thrombus extraction device further comprises advancing an intermediate shaft distally until the coring portion of the thrombus extraction device is beyond the distal end of the catheter, wherein the intermediate shaft slidably extends through the catheter and a distal end thereof is coupled to a proximal end of the coring portion, locking the intermediate shaft with respect to the catheter, retracting an inner shaft with respect to the catheter and the intermediate shaft until a stop feature fixed on the inner shaft engages a corresponding feature on the coring portion for further expansion of the thrombus extraction device to the expanded state, and dynamically coupling the inner shaft with respect to the intermediate shaft retracting the thrombus extraction device proximally so that the coring portion cores and separates the portion of the vascular thrombus from a venous vessel wall while the mesh structure captures the vascular thrombus portion, wherein the coring portion maintains sufficient radial force on the venous vessel wall to core and separate the vascular thrombus portion in the expanded state; and withdrawing the thrombus extraction device from the patient.

24. The method of claim 23, wherein deploying the thrombus extraction device further comprises determining a position of the thrombus extraction device with respect to the catheter via imaging of a first radiopaque marker located on the catheter and a second radiopaque marker located on at least one of the intermediate shaft, the inner shaft, coring portion, or mesh structure.

25. A thrombus extraction device for removal of a vascular thrombus from a blood vessel of a patient, the thrombus extraction device comprising:

a catheter having a proximal end and a distal end, an outer shaft defining a first lumen, an intermediate shaft defining a second lumen, and an inner shaft, where the intermediate shaft is coaxial the first lumen and the inner shaft is coaxial the second lumen;

a proximal self-expanding coring element having a proximal end and a distal end and configured to core and separate a portion of the vascular thrombus from the blood vessel, wherein the proximal end of the coring element is coupled to the distal end of the intermediate shaft; and a distal expandable cylindrical portion formed of a filament mesh structure having a proximal end and a distal end and configured to capture the vascular thrombus portion, wherein the mesh structure filaments are interwoven with the coring element so that the proximal end of the mesh structure is attached to the distal end of the coring element, and wherein the distal end of the mesh structure is coupled to the distal end of the inner shaft.

26. The thrombus extraction device of claim 25, wherein the coring element and the mesh structure are receivable within the outer shaft, and wherein the coring element and mesh structure are in a constrained configuration when received within the outer shaft and an expanded configuration when free of the constraining outer shaft.

27. The thrombus extraction device of claim 26, wherein the coring element defines a coring angle in a range between about 20 degrees and about 50 degrees when the thrombus extraction device is in the expanded configuration, wherein the coring portion is configured to maintain sufficient radial force on the venous vessel wall to core and separate the vascular thrombus portion in the expanded configuration.

28. A thrombectomy system comprising the thrombus extraction device of claim 25, and the system further comprising a self-expanding funnel coupled to a distal end of an introducer sheath and an elongate obturator comprising a capture sheath feature configured to retain the self-expanding funnel in a constrained configuration.

\* \* \* \* \*